US008568731B2

(12) United States Patent
Foster et al.

(10) Patent No.: US 8,568,731 B2
(45) Date of Patent: Oct. 29, 2013

(54) STAPHYLOCOCCUS AUREUS ANTIGENIC POLYPEPTIDES AND COMPOSITIONS

(75) Inventors: Simon Foster, Hathersage (GB); Philip McDowell, Mapperley (GB); Kirsty Brummell, West Bridgford (GB); Simon Clarke, Sheffield (GB)

(73) Assignee: Biosynexus Incorporated, Gaithersburg, MD (US)

( * ) Notice: Subject to any disclaimer, the term of this patent is extended or adjusted under 35 U.S.C. 154(b) by 389 days.

(21) Appl. No.: 12/555,626

(22) Filed: Sep. 8, 2009

(65) Prior Publication Data

US 2010/0166792 A1    Jul. 1, 2010

Related U.S. Application Data

(62) Division of application No. 11/256,173, filed on Oct. 24, 2005, now Pat. No. 7,585,658, which is a division of application No. 10/311,879, filed as application No. PCT/GB01/02685 on Jun. 20, 2001, now abandoned.

(30) Foreign Application Priority Data

Jun. 20, 2000    (GB) .................................. 0014907.0

(51) Int. Cl.
*A61K 39/02* (2006.01)
*A61K 39/085* (2006.01)
*C07K 14/195* (2006.01)

(52) U.S. Cl.
USPC .................. 424/190.1; 424/184.1; 424/243.1; 530/350

(58) Field of Classification Search
None
See application file for complete search history.

(56) References Cited

U.S. PATENT DOCUMENTS

| 4,425,330 | A |   | 1/1984  | Norcross et al. |
|-----------|---|---|---------|-----------------|
| 5,807,978 | A | * | 9/1998  | Kokolus et al. ............... 530/300 |
| 6,008,341 | A |   | 12/1999 | Foster |
| 6,617,156 | B1| * | 9/2003  | Doucette-Stamm et al. ........................ 435/320.1 |

FOREIGN PATENT DOCUMENTS

| EP | 0786519 A2 | 7/1997 |
| WO | 93/07487 | 4/1993 |
| WO | 97/14801 | 4/1997 |
| WO | 97/43314 | 11/1997 |
| WO | WO 99/50418 | 10/1999 |

OTHER PUBLICATIONS

Cancer Immunity 2002, vol. 2: 5.*
Houghten et al. (Vaccines, 1986, Edited by Fred Brown: Cold Spring Harbor Laboratory).*
Holmes, Exp. Opin.Invest. Drugs, 2001, 10(3):511-519.*
Greenspan et al (Nature Biotechnology, 1999, 7:936-937).*
Blythe et al, Protein Science 14:246-248, 2005.*
Greenbaum et al, Journal of Molecular Recognition, 20(2):75-82, 2007.*
Database EMBL [Online] Jul. 3, 2000, "*Staphylococcus aureus* sai-1 gene for 29-kDa cell surface protein, complete cds." XP002445369 retrieved from EBI accession No. EMBL:AB042826 Database accession No. AB042826.
Lederman et al (Molecular Immunology 28:1171-1181, 1991).
Li et al (Proc. Natl. Acad. Sci. USA 77:3211-3214, 1980).
Cancer Immunity, vol. 2, p. 5 (Jun. 28, 2002).
Spencer, et al 1990 Dev. Biol. 139, 279-291.
XP-002278160; Kuroda, M., et al., "Whole Genome Sequencing of Meticillin-Resistant *Staphylococcus aureus*," *Lancet*, 357:1225-1240 (2001).
XP-002278159; Foster, Simon, "Molecular Characterization and Functional Analysis of the Major Autolysin of *Staphylococcus aureus* 8325/4." *J. of Bacteriology*, 177(19):5723-5725 (1995).
XP-002278161; Kuroda, M., et al., "Nucleotide Substitutions in *Staphylococcus aureus* Strains," *DNA Res.*, 11:51-56 (2004).
XP-002278162; Kuroda, M., et al., "Whole Geneom Sequencing of Meticillin-Resistant *Staphylococcus aureaus*," *Lancet*, 357:1225-1240 (2001).
Rahman et al., "Gamma Hemolysin genes in the same family with LukF and lukS genes in methicillin resistant *Staphylococcus aureus*," *Bioscience Biotechnology Biochemistry*, 57(7):1234-1236 (1993).
International Search Report, Sep. 18, 2001.
Foster, Simon, "Molecular Characterization and Functional Analysis of the Major Autolysin of *Staphylococcus aureus* 8325/4," *J. of Bacteriology*, 177(19):5723-5725 (1995).
*Cancer Immunity*, 2:5 (Jun. 28, 2002).
*Infect. Immun.*, 62(5):1843-7 (1994).
Rudinger et al., "Peptide Hormones," Parsons, J.A., University Park Press, 1976 pg.
Burgess et al., *J. Cell Biology*, 111:2129-2138 (1990).
Lazar et al., *Molecular and Cellular Biology* 8(3);1247-1252 (1988).
Jobling et al., *Mol. Microbiol.*, 5(7):1755-67 (1991).
Oshida et al., *Proc. Natl. Acad. Sci.*, 92(1):285-289 (1995).
WISE "The development of new antimicrobial agents" 1998 BMJ Sep. 5;317(7159):643-4.
Projan SJ, Novick, RP. The molecular basis of pathogenicity. In: Crossley KB, Archer GL eds. The Staphylococci in Human Disease. New York: Churchill Livingstone, 1997; 55-81. [book, no copy available].
Cooney et al., "The Gamma-Hemolysin Locus of Staphylococcus aureus Comprises Three Linked Genes, Two of Which Are Identical to the Genes for the F and S Components of Leukocidin" Infection and Immunity, 1993, vol. 61, No. 2, pp. 768-771.
Bowie et al., Deciphering the message in protein sequences: tolerate to amino acid substitutions, Science, 1990, vol. 247, pp. 1306-1310.

* cited by examiner

*Primary Examiner* — Padma Baskar
(74) *Attorney, Agent, or Firm* — Casimir Jones, S.C.; Tyler J. Sisk

(57) ABSTRACT

The invention relates to a method for the identification of antigenic polypeptides expressed by pathogenic microbes; vaccines comprising the polypeptides; recombinant methods to manufacture the polypeptides; and therapeutic antibodies directed to the polypeptides.

7 Claims, No Drawings

STAPHYLOCOCCUS AUREUS ANTIGENIC POLYPEPTIDES AND COMPOSITIONS

This application is a divisional application of U.S. patent application Ser. No. 11/256,173, filed Oct. 24, 2005, issued as U.S. Pat. No. 7,585,658on Sep. 8, 2009, which is a divisional application of U.S. patent application Ser. No. 10/311,879, filed Mar. 18, 2003, now abandoned, which is a national stage application of PCT/GB01/02685, filed Jun. 20, 2001, which claims the benefit of priority of Great Britain Application No. GB 0014907.0, filed Jun. 20, 2000, each of which is herein incorporated by reference in its entirety.

The invention relates to a method for the identification of antigenic polypeptides expressed by pathogenic microbes; vaccines comprising said polypeptides; recombinant methods to manufacture said polypeptides; and therapeutic antibodies directed to said polypeptides.

Microbial organisms cause a number of fatal or debilitating diseases which affect many millions of people around the world. Currently methods to control microbial organisms include the use of antimicrobial agents (antibiotics) and disinfectants. These have proved to be problematic since exposure to these agents places a significant selection pressure resulting in the creation of resistant microbes which can avoid the effects of the antimicrobial agent(s). For example, recently it has been discovered that microbial organisms have become resistant to triclosan, an agent added to many disinfectants used in households and industrial environments.

An arguably greater problem is the evolution of antibiotic resistant strains of a number of significant pathogenic microbes.

For example, and not by way of limitation, it is estimated that there are up to 50 million people world-wide infected with drug resistant tuberculosis (TB) (Figures from the World Health Organisation, 1998). In the past the use of antibiotics to treat TB relied on the administration of single drugs (eg ethionamide) which promoted a relatively high frequency of resistance. For this reason, combinations of drugs are now used to treat tuberculosis. However the fatality rate in cases caused by strains that are resistant to at least one drug used to treat tuberculosis still approaches 50% even when treatment is given. *Mycobacterium tuberculosis*, the causative agent of TB, is a slow growing bacteria and takes a long time to kill. Therefore, for a drug combination to be effective a person with TB must take the drug combination daily for at least six months. Accordingly, patients frequently have to take two or more pills daily and this requires a regimented dosage over a relatively long period of treatment. Many patients take the medications only intermittently and therefore do not finish the full course of therapy to completely eradicate the *M. tuberculosis* infection. Moreover, TB is strongly associated with HIV infection and therefore the establishment of TB is strongly correlated with immunosuppression.

Vaccination against TB has been available for many years. The *bacillus* calmette and guerin (BCG) vaccination has been widely used throughout the world for a long time because it is a safe and inexpensive means to vaccinate large numbers of people who potentially could contract TB. BCG is derived from live, attenuated strains of *Mycobacterium bovis*. However the impact of vaccination on the infectious forms of TB is minimal and BCG has therefore contributed little to the overall control of the disease.

A further example of a pathogenic organism which has developed resistance to antibiotics is *Staphylococcus aureus*. *S. aureus* is a bacterium whose normal habitat is the epithelial lining of the nose in about 20-40% of normal healthy people and is also commonly found on people's skin usually without causing harm. However, in certain circumstances, particularly when skin is damaged, this germ can cause infection. This is a particular problem in hospitals where patients may have surgical procedures and/or be taking immunosuppressive drugs. These patients are much more vulnerable to infection with *S. aureus* because of the treatment they have received. Resistant strains of *S. aureus* have arisen in recent years. Methicillin resistant strains are prevalent and many of these resistant strains are also resistant to several other antibiotics. Currently there is no effective vaccination procedure for *S. aureus*. In the US, *S. aureus* infections are the cause of 13% of the two million hospitalised infections each year. This represents 260,000 people with an infection of *S. aureus*, of which 60-80,000 die.

*S. aureus* is therefore a major human pathogen capable of causing a wide range of life threatening diseases including septicaemia, endocarditis, arthritis and toxic shock. This ability is determined by the versatility of the organism and its arsenal of components involved in virulence. Pathogenicity is multifactorial and no one component has shown to be responsible for a particular infection, see Projan, S. J. & Novick, R. P. (1997) in The Staphylococci in Human Disease (Crossley, K. B. & Archer, G. L., eds.) pp. 55-81.

At the onset of infection, and as it progresses, the needs and environment of the organism changes and this is mirrored by a corresponding alteration in the virulence determinants which *S. aureus* produces. At the beginning of infection it is important for the pathogen to adhere to host tissues and so a large repertoire of cell surface associated attachment proteins are made. These include collagen-, fibrinogen- and fibronectin-binding proteins. The pathogen also has the ability to evade host defences by the production of factors that reduce phagocytosis or interfere with the ability of the cells to be recognised by circulating antibodies.

Often a focus of infection develops as an abscess and the number of organisms increases. *S. aureus* has the ability to monitor its own cell density by the production of a quorum sensing peptide. Accumulation of the peptide, associated with physiological changes brought about by the beginning of starvation of the cells, elicits a switch in virulence determinant production from adhesins to components involved in invasion and tissue penetration. These include a wide range of hemolysins, proteases and other degradative enzymes.

During the process of any infection the virulence determinants made by *S. aureus* are produced in response to environmental and physiological stimuli. These stimuli will be dependent on the niche within the body and will change as the infection progresses. Little is known of the conditions in vivo and it is likely that some components are produced solely in this environment. These are therefore potential vaccine components, which could not be discovered by previous techniques.

One of the most important developments in recent medical history is the development of vaccines which provide prophylactic protection from a wide variety of pathogenic organisms. Many vaccines are produced by inactivated or attenuated pathogens which are injected into an individual. The immunised individual responds by producing both a humoral (antibody) and cellular (cytolytic T cells, CTL's) response. For example, hepatitis vaccines are made by heat inactivating the virus and treating it with a cross linking agent such as formaldehyde. An example of an attenuated pathogen useful as a vaccine is represented by polio vaccines which are produced by attenuating a live pathogen.

However the use of attenuated organisms in vaccines for certain diseases is problematic due to the lack of knowledge regarding the pathology of the condition and the nature of the attenuation. For certain viral agents this is a particular problem since viruses, in particular retroviruses, have an error prone replication cycle which results viable mutations in the genes which comprise the virus. This can result in alterations to antigenic determinants which have previously been used as vaccines. An alternative to the use of inactivated or attenuated pathogens is the identification of pathogen epitopes to which the immune system is particularly sensitive. In this regard many pathogenic toxins produced by pathogenic organisms during an infection are particularly useful in the development of vaccines which protect the individual from a particular pathogenic organism.

The development of so-called subunit vaccines (vaccines in which the immunogen is a fragment or subunit of a protein or complex expressed by a particular pathogenic organism) has been the focus of considerable medical research. The need to identify candidate molecules useful in the development of subunit vaccines is apparent not least because conventional chemotherapeutic approaches to the control of pathogenic organisms has more recently been stymied by the development of antibiotic resistance. A number of methods have been developed to identify potential antigenic polypeptides which can be used as a vaccine. One such method is disclosed herein.

It has been known for many years that tumour cells produce a number of tumour cell specific antigens, some of which are presented at the tumour cell surface. The immune system recognises these antigens as foreign thereby resulting in the production of antibodies to self antigens, so called autoantibodies or autologous antisera.

One such technique is Serological identification of antigens by recombinant Expression Cloning, abbreviated to SEREX.

Typically, the technique involves the extraction of RNA from tumour tissue followed by the selective enrichment of mRNA from the isolated total RNA. The mRNA is reverse transcribed into cDNA using viral reverse transcriptase. The cDNA thus synthesised is subcloned into an expression vector and transformed into an appropriate bacterial strain. The transformed bacteria are plated onto a suitable nutrient agar and under appropriate growth conditions the subcloned cDNA is expressed from the expression vector in the bacterial cell. The cells are lysed naturally by the use of phage based expression vectors, for example λ phage or phagemid based vectors, which through their lytic cycle cause cell lysis. The released polypeptides are transferred to a suitable membrane support (i.e. nitrocellulose, nylon) and exposed to autologous antisera from the patient from which the tumour tissue was originally isolated. The immunoscreening methodology allows the identification of genes that are over expressed or inappropriately expressed in a selected tumour tissue from a patient.

We have exploited this technique to identify antigenic polypeptides expressed by pathogenic organisms during an infection. Autologous antisera produced during the infection is used to screen an expression library created from genomic DNA to identify and clone antigens.

In its broadest aspect the invention relates to the identification of antigenic polypeptides expressed during an infection by a pathogenic microbe.

According to a first aspect of the invention there is provided a method to identify antigenic polypeptides comprising:
(i) providing a nucleic acid library encoding genes or partial gene sequences of a pathogenic organism;
(ii) transforming/transfecting said library into a host cell;
(iii) providing conditions conducive to the expression of said transformed/transfected genes or partial gene sequences;
(iv) contacting the polypeptides expressed by the genes/partial gene sequences with autologous antisera derived from an animal infected with, or has been infected with, said pathogenic organism; and
(v) purifying the nucleic acid encoding the polypeptide or partial polypeptide binding to said autologous antisera.

In a preferred method of the invention said library comprises genomic DNA of a pathogenic organism.

Ideally said pathogenic organism is bacterial.

More preferably still said bacterial organism is selected from the following: *Staphylococcus aureus*; *Staphylococcus epidermidis*; *Enterococcus faecalis*; *Mycobacterium tuberculsis*; *Streptococcus* group B; *Streptoccocus pneumoniae*; *Helicobacter pylori*; *Neisseria gonorrhea*; *Streptococcus* group A; *Borrelia burgdorferi*; *Coccidiodes immitis*; *Histoplasma sapsulatum*; *Neisseria meningitidis* type B; *Shigella flexneri*; *Escherichia coli*; *Haemophilus influenzae*.

Preferably still said pathogenic organism is of the genus *Staphylococcus* spp. Ideally organism is *Staphylococcus aureus* or *Staphylococcus epidermidis*.

In a further preferred embodiment of the invention said nucleic acid library is a lambda library, ideally a lambda expression library.

According to a second aspect of the invention there is provided a nucleic acid molecule comprising a DNA sequence selected from:
(i) the DNA sequence as represented in SEQ ID NO's 1-13;
(ii) DNA sequences which hybridise to the sequence presented in the SEQ ID No's 1-13 identified in (i) above which encode a polypeptide expressed by a pathogenic organism and
(iii) DNA sequences which are degenerate as a result of the genetic code to the DNA sequences defined in (i) and (ii).

In a yet still further preferred embodiment of the invention said nucleic acid molecule
is genomic DNA.

In a preferred embodiment of the invention there is provided an isolated nucleic acid molecule which anneals under stringent hybridisation conditions to the sequences presented in SEQ ID NO's 1-13.

Stringent hybridisation/washing conditions are well known in the art. For example, nucleic acid hybrids that are stable after washing in 0.1×SSC, 0.1% SDS at 60° C. It is well known in the art that optimal hybridisation conditions can be calculated if the sequences of the nucleic acid is known. For example, hybridisation conditions can be determined by the GC content of the nucleic acid subject to hybridisation. Please see Sambrook et al (1989) Molecular Cloning; A Laboratory Approach. A common formula for calculating the stringency conditions required to achieve hybridisation between nucleic acid molecules of a specified homology is:

$$T_m = 81.5° C. + 16.6 \text{ Log } [Na^+] + 0.41 [\% \text{ G}+\text{C}] - 0.63 (\% \text{ formamide}).$$

According to a third aspect of the invention there is provided at least one polypeptide identified by the method according to the invention.

In a preferred embodiment of the invention, said polypeptide is associated with infective pathogenicity of an organism according to any previous aspect or embodiment of the invention.

More preferably still said polypeptide is at least one, or part of SEQ ID NOs: 14-32.

According to a fourth aspect of the invention there is provided a nucleic acid molecule characterised in that said nucleic acid molecule is part of a vector adapted to facilitate recombinant expression of the polypeptide encoded by said nucleic acid molecule.

In a preferred embodiment of the invention said vector is an expression vector adapted for prokaryotic gene expression. Alternatively said expression vector is adapted for eukaryotic gene expression.

Typically said adaptation includes, by example and not by way of limitation, the provision of transcription control sequences (promoter sequences) which mediate cell specific expression. These promoter sequences may be cell specific, inducible or constitutive.

Promoter is an art recognised term and, for the sake of clarity, includes the following features which are provided by example only, and not by way of limitation. Enhancer elements are cis acting nucleic acid sequences often found 5' to the transcription initiation site of a gene (enhancers can also be found 3' to a gene sequence or even located in intronic sequences and is therefore position independent). Enhancers function to increase the rate of transcription of the gene to which the enhancer is linked. Enhancer activity is responsive to trans acting transcription factors (polypeptides) which have been shown to bind specifically to enhancer elements. The binding/activity of transcription factors (please see Eukaryotic Transcription Factors, by David S Latchman, Academic Press Ltd, San Diego) is responsive to a number of environmental cues which include, by example and not by way of limitation, intermediary metabolites (eg glucose, lipids), environmental effectors (eg light, heat,).

Promoter elements also include so called TATA box and RNA polymerase initiation selection (RIS) sequences which function to select a site of transcription initiation. These sequences also bind polypeptides which function, inter alia, to facilitate transcription initiation selection by RNA polymerase.

Adaptations also include the provision of selectable markers and autonomous replication sequences which both facilitate the maintenance of said vector in either the eukaryotic cell or prokaryotic host. Vectors which are maintained autonomously are referred to as episomal vectors.

Adaptations which facilitate the expression of vector encoded genes include the provision of transcription termination/polyadenylation sequences. This also includes the provision of internal ribosome entry sites (IRES) which function to maximise expression of vector encoded genes arranged in bicistronic or multi-cistronic expression cassettes.

These adaptations are well known in the art. There is a significant amount of published literature with respect to expression vector construction and recombinant DNA techniques in general. Please see, Sambrook et al (1989) Molecular Cloning: A Laboratory Manual, Cold Spring Harbour Laboratory, Cold Spring Harbour, N.Y. and references therein; Marston, F (1987) DNA Cloning Techniques: A Practical Approach Vol III IRL Press, Oxford UK; DNA Cloning: F M Ausubel et al, Current Protocols in Molecular Biology, John Wiley & Sons, Inc. (1994).

According to yet a further aspect of the invention there is provided a method for the production of the polypeptides according to any previous aspect or embodiment of the invention comprising:
(i) providing a cell transformed/transfected with a vector according to the invention;
(ii) growing said cell in conditions conducive to the manufacture of said polypeptides; and
(iii) purifying said polypeptide from said cell, or its growth environment.

In a preferred method of the invention said vector encodes, and thus said recombinant polypeptide is provided with, a secretion signal to facilitate purification of said polypeptide.

According to a fifth aspect of the invention there is provided a cell or cell-line transformed or transfected with the vector according to the invention.

In a preferred embodiment of the invention said cell is a prokaryotic cell. Alternatively said cell is a eukaryotic cell selected from: fungal, insect, amphibian; mammalian; plant.

According to a yet further aspect of the invention there is provided a vaccine comprising at least one polypeptide according to the invention.

Ideally said vaccine further comprises a carrier and/or adjuvant.

The terms adjuvant and carrier are construed in the following manner Some polypeptide or peptide antigens contain B-cell epitopes but no T cell epitopes. Immune responses can be greatly enhanced by the inclusion of a T cell epitope in the polypeptide/peptide or by the conjugation of the polypeptide/peptide to an immunogenic carrier protein such as key hole limpet haemocyanin or tetanus toxoid which contain multiple T cell epitopes. The conjugate is taken up by antigen presenting cells, processed and presented by human leukocyte antigens (HLA's) class II molecules. This allows T cell help to be given by T cell's specific for carrier derived epitopes to the B cell which is specific for the original antigenic polypeptide/peptide. This can lead to increase in antibody production, secretion and isotype switching.

An adjuvant is a substance or procedure which augments specific immune responses to antigens by modulating the activity of immune cells. Examples of adjuvants include, by example only, agonsitic antibodies to co-stimulatory molecules, Freunds adjuvant, muramyl dipeptides, liposomes. An adjuvant is therefore an immunomodulator. A carrier is an immunogenic molecule which, when bound to a second molecule augments immune responses to the latter.

In yet a further aspect of the invention there is provided a method to immunise an animal against a pathogenic microbe comprising administering to said animal at least one polypeptide, or part thereof, according to the invention or the vaccine according to the invention.

In a preferred method of the invention said animal is human.

Preferably the vaccine, or antigenic polypeptide, can be delivered by direct injection either intravenously, intramuscularly, subcutaneously. Further still, the vaccine or antigenic polypeptide, may be taken orally.

Preferably the vaccine is against the bacterial species *Staphylococcus aureus*.

The vaccine may also be against the bacterial species *Staphylococcus epidermidis*.

It will also be apparent that vaccines or antigenic polypeptides are effective at preventing or alleviating conditions in animals other than humans, for example and not by way of limitation, family pets, livestock, horses.

According to a further aspect of the invention there is provided an antibody, or at least an effective binding part thereof, which binds at least one polypeptide according to the invention.

In a preferred embodiment of the invention said antibody is a polyclonal or monoclonal antibody wherein said antibody is specific to said polypeptide.

Alternatively, said antibody is a chimeric antibody produced by recombinant methods to contain the variable region of said antibody with an invariant or constant region of a human antibody.

In a further alternative embodiment of the invention, said antibody is humanised by recombinant methods to combine the complimentarity determining regions of said antibody with both the constant (C) regions and the framework regions from the variable (V) regions of a human antibody.

Preferably said antibody is provided with a marker including a conventional label or tag, for example a radioactive and/or fluorescent and/or epitope label or tag.

Preferably said humanised monoclonal antibody to said polypeptide is produced as a fusion polypeptide in an expression vector suitably adapted for transfection or transformation of prokaryotic or eukaryotic cells.

Antibodies, also known as immunoglobulins, are protein molecules which have specificity for foreign molecules (antigens) Immunoglobulins (Ig) are a class of structurally related proteins consisting of two pairs of polypeptide chains, one pair of light (L) (low molecular weight) chain ($\kappa$ or $\lambda$), and one pair of heavy (H) chains ($\gamma$, $\alpha$, $\mu$, $\delta$ and $\epsilon$), all four linked together by disulphide bonds. Both H and L chains have regions that contribute to the binding of antigen and that are highly variable from one Ig molecule to another. In addition, H and L chains contain regions that are non-variable or constant.

The L chains consist of two domains. The carboxy-terminal domain is essentially identical among L chains of a given type and is referred to as the "constant" (C) region. The amino terminal domain varies from L chain to L chain and contributes to the binding site of the antibody. Because of its variability, it is referred to as the "variable" (V) region.

The H chains of Ig molecules are of several classes, $\alpha$, $\mu$, $\sigma$, $\alpha$, and $\gamma$ (of which there are several sub-classes). An assembled Ig molecule consisting of one or more units of two identical H and L chains, derives its name from the H chain that it possesses. Thus, there are five Ig isotypes: IgA, IgM, IgD, IgE and IgG (with four sub-classes based on the differences in the H chains, i.e., IgG1, IgG2, IgG3 and IgG4). Further detail regarding antibody structure and their various functions can be found in, Using Antibodies: A laboratory manual, Cold Spring Harbour Laboratory Press.

Chimeric antibodies are recombinant antibodies in which all of the V-regions of a mouse or rat antibody are combined with human antibody C-regions. Humanised antibodies are recombinant hybrid antibodies which fuse the complimentarity determining regions from a rodent antibody V-region with the framework regions from the human antibody V-regions. The C-regions from the human antibody are also used. The complimentarity determining regions (CDRs) are the regions within the N-terminal domain of both the heavy and light chain of the antibody to where the majority of the variation of the V-region is restricted. These regions form loops at the surface of the antibody molecule. These loops provide the binding surface between the antibody and antigen.

Antibodies from non-human animals provoke an immune response to the foreign antibody and its removal from the circulation. Both chimeric and humanised antibodies have reduced antigenicity when injected to a human subject because there is a reduced amount of rodent (i.e. foreign) antibody within the recombinant hybrid antibody, while the human antibody regions do not illicit an immune response. This results in a weaker immune response and a decrease in the clearance of the antibody. This is clearly desirable when using therapeutic antibodies in the treatment of human diseases. Humanised antibodies are designed to have less "foreign" antibody regions and are therefore thought to be less immunogenic than chimeric antibodies.

In another aspect of the invention there is provided a vector which is adapted for the expression of the humanised or chimeric antibodies according to the invention.

In a yet further aspect of the invention, there is provided a cell or cell line which has been transformed or transfected with the vector encoding the humanised or chimeric antibody according to the invention.

In a yet further aspect of the invention there is provided a method for the production of the humanised or chimeric antibody according to the invention comprising:
(i) providing a cell transformed or transfected with a vector which comprises a nucleic acid molecule encoding the humanised or chimeric antibody according to the invention;
(ii) growing said cell in conditions conducive to the manufacture of said antibody; and
(iii) purifying said antibody from said cell, or its growth environment.

In a yet further aspect of the invention there is provided a hybridoma cell line which produces a monoclonal antibody as hereinbefore described.

In a further aspect of the invention there is provided a method of producing monoclonal antibodies according to the invention using hybridoma cell lines according to the invention.

In a further aspect of the invention there is provided a method for preparing a hybridoma cell-line producing monoclonal antibodies according to the invention comprising the steps of:
i) immunising an immunocompetent mammal with an immunogen comprising at least one polypeptide having the amino acid sequence as represented in SEQ. ID No 14-32, or fragments thereof;
ii) fusing lymphocytes of the immunised immunocompetent mammal with myeloma cells to form hybridoma cells;
iii) screening monoclonal antibodies produced by the hybridoma cells of step (ii) for binding activity to the amino acid sequences of (i);
iv) culturing the hybridoma cells to proliferate and/or to secrete said monoclonal antibody; and
v) recovering the monoclonal antibody from the culture supernatant.

Preferably, the said immunocompetent mammal is a mouse. Alternatively, said immunocompetent mammal is a rat.

The production of monoclonal antibodies using hybridoma cells is well-known in the art. The methods used to produce monoclonal antibodies are disclosed by Kohler and Milstein in Nature 256, 495-497 (1975) and also by Donillard and Hoffman, "Basic Facts about Hybridomas" in Compendium of Immunology V.II ed. by Schwartz, 1981, which are incorporated by reference.

In a further aspect of the invention there is provided the use of the antibodies for manufacture of a medicament for the treatment of *Staphylococcus aureus*-associated septicaemia, food-poisoning or skin disorders.

In another aspect of the invention there is provided the use of the antibodies according to the invention for the manufacture of a medicament for the treatment of *Staphylococcus epidermidis*-associated septicaemia, peritonitis or endocarditis.

It will be apparent that the polypeptides identified by the method according to the invention will facilitate the production of therapeutic antibodies to a range of diseases resulting from pathogenic infection, for example, septicaemia; tuberculosis; bacteria-associated food poisoning; blood infections;

peritonitis; endocarditis; sepsis; meningitis; pneumonia; stomach ulcers; gonorrhoea; strep throat; streptococcal-associated toxic shock; necrotizing fasciitis; impetigo; histoplasmosis; Lyme disease; gastro-enteritis; dysentery; shigellosis.

As has already been stated earlier, microbial organisms cause a wide variety of diseases. Listed below, and not by way of limitation, are a number of micro-organisms and some of the diseases they cause.

| Micro-organism | Disease(s) caused |
| --- | --- |
| Staphylococcus aureus | Sepsis, food poisoning, septicaemia, |
| Staphylococcus epidermidis | Peritonitis, septicaemia, endocarditis, other hospital-associated diseases |
| Enterococcus faecalis | Endocarditis, cystitis, wound infections |
| Mycobacterium tuberculosis | Tuberculosis |
| Streptococcus group B | Sepsis, meningitis, pneumonia, bladder infections |
| Streptococcus pneumoniae | Pneumonia, meningitis |
| Helicobacter pylori | Stomach ulcers |
| Neisseria gonorrhoeae | Gonorrhoea |
| Streptococcus group A | Strep throat, necrotizing fasciitis, impetigo, Strep. Toxic shock syndrome |
| Borrelia burgdoferi | Lyme disease |
| Coccidiodes immitis | Pneumonia |
| Histoplasma sapsulatum | Histoplasmosis, pneumonia |
| Neisseria meningitidis type B | Meningitis |
| Shigella flexneri | Gastro-enteritis, shigellosis, dysentry |
| Escherichia coli | Food-poisoning, gastro-enteritis |
| Haemophilus influenzae | Meningitis, pneumonia, arthritis, cellulitis |

An embodiment of the invention will now be described by example only and with reference to the following materials, methods and SEQ ID NO's 1-19 and Table 1.

Materials and Methods

A λZAP Express library of genomic DNA of *S. aureus* 8325/4 was used. It contains fragments of 2-10 kb from a partial Sau3A digest of total genomic DNA. This was cloned into the BamH1 site of the vector. The library contains >10× coverage of the genome. The library was probed by plaque lift using an initial screen of approximately 20,000 plaque forming units on a 9 cm diameter Petri dish. The plating cells used, their treatment, the plating procedure and buffers were exactly as described in the manufacturers handbook (Stratagene). Plating cells, *Escherichia coli* XL1-Blue MRF', were infected with phage and plated in 3 ml top LB agar containing 10 mM MgSO$_4$ onto LB plates containing 10 mM MgSO$_4$. The plates were then incubated at 42° C. for 4 hr. An 8.5 cm diameter nitrocellulose filter disc (previously soaked in 10 mM IPTG and air-dried) was placed on each plate and its location marked. The plates were then incubated for a further 3.5 hr at 37° C. The filters were removed and washed in TBST buffer before blocking overnight at 4° C. in TBST containing 6% w/v dried skimmed milk and 3% v/v pig serum (Sigma). The serum was used to block any Protein A clones on the filter. The filters are then treated with patient serum (1/5000 dilution) in blocking solution for 90 min at room temperature. Antisera have been obtained from patients convalescing from major *S. aureus* infections. The filters are then washed for 3×10 min in TBST. Secondary antibody used was goat anti-human whole IgG alkaline phosphatase linked (Sigma) at 1/30,000 dilution in blocking solution at room temperature for 30 min. The filters were then washed as above and developed using a standard colorimetric procedure.

Cross-reactive plaques were located on the agar plates and cored into 0.2 ml phage buffer with 0.02 ml chloroform. The titre of each core stock was determined and the phage plated at approximately 200 plaques per plate. A plaque lift and screen was performed as above to give single, pure cross-reactive clones.

The pure clones were then spotted (1 µl) onto plates to give a confluent plaque of 0.5 cm diameter. 30 individual clones can be spotted on each plate. A plaque lift is performed and the filter probed with an appropriate sera. In this way clones can be tested for their cross-reactivity with other patient sera, non-infected donor sera and anti-Protein A sera.

Individual clones were then excised to give a phagemid in *E. coli* XLOLR using the manufacturers protocol (Stratagene). A plasmid miniprep of each was carried out and the size of the genomic insert determined by restriction mapping. The identity of the cloned insert was determined by DNA sequencing using primers against vector sequence, which allows sequencing across the insert. By comparison of the derived sequence against the public domain databases the nature of the cloned gene(s) can be determined Hybridisation Solutions/Conditions Typically, hybridisation conditions uses 4-6×SSPE (20× SSPE contains 175.3 g NaCl, 88.2 g NaH$_2$PO$_4$H$_2$O and 7.4 g EDTA dissolved to 1 litre and the pH adjusted to 7.4); 5-10× Denhardts solution (50×Denhardts solution contains 5 g Ficoll (type 400, Pharmacia), 5 g polyvinylpyrrolidone abd 5 g bovine serum albumen; 100 µg-1.0 mg/ml sonicated salmon/herring DNA; 0.1-1.0% sodium dodecyl sulphate; optionally 40-60% deionised formamide. Hybridisation temperature will vary depending on the GC content of the nucleic acid target sequence but will typically be between 42°-65° C.

*Staphylococcus aureus* clones identified in human sera screen

TABLE 1

| Patient Sera | Clone | Encoded proteins | Locus number |
| --- | --- | --- | --- |
| A | 1 | γ hemolysin B and C subunit | 1 |
| A | 3 | Atl | 2 |
| A | 4 | γ hemolysin B and C subunit | 1 |
| A | 5 | γ hemolysin B and C subunit | 1 |
| A | 7 | Novel putative protease (ORF1 novel antigen like) | 7 |
| A | 8 | Novel nuclease (YisK) | 5 |
| A | 9 | Novel autolysin | 6 |
| A | 10 | γ hemolysin B and C subunit | 1 |
| A | 11 | Atl | 2 |
| A | 14 | γ hemolysin B and C subunit | 1 |
| A | 15 | γ hemolysin B and C subunit | 1 |
| A | S1 | Novel putative protease (ORF1 novel antigen like) | 7 |
| A | S5 | Novel surface protein | 12 |
| A | S17 | γ hemolysin B and C subunit | 1 |
| A | S18 | Novel putative protease (ORF1 novel antigen like) | 7 |
| A | S19 | Novel autolysin | 6 |
| A | S20 | Novel surface protein/toxin | 13 |
| A | S21 | γ hemolysin B and C subunit | 1 |
| A | S25 | γ hemolysin B and C subunit | 1 |
| A | S29 | Fibrinogen binding protein) | 3 |
| A | S44 | Novel surface protein | 12 |
| A | S45 | Atl | 2 |
| A | S55 | Atl | 2 |
| A | S64 | Atl | 2 |
| A | S66 | Atl | 2 |
| B | 2 | Novel exotoxin (exotoxin 2 like) | 8 |
| C | 1 | Coagulase | 4 |
| C | 2 | Coagulase | 4 |
| C | 3 | Coagulase | 4 |
| C | 4 | Coagulase | 4 |
| C | 5 | Coagulase | 4 |
| C | 6 | Coagulase | 4 |
| C | 7 | Coagulase | 4 |
| C | 8 | Coagulase | 4 |

TABLE 1-continued

| Patient Sera | Clone | Encoded proteins | Locus number |
|---|---|---|---|
| C | 9 | Coagulase | 4 |
| C | 10 | Coagulase | 4 |
| C | 11 | Coagulase | 4 |
| C | 13 | Coagulase | 4 |
| C | 14 | Coagulase | 4 |
| C | 15 | Coagulase | 4 |
| C | 19 | Coagulase | 4 |
| C | 20 | Coagulase | 4 |
| C | 25 | Coagulase | 4 |

TABLE 1-continued

| Patient Sera | Clone | Encoded proteins | Locus number |
|---|---|---|---|
| E | 6 | Novel surface proteins | 9/10 |
| E | 7 | Novel surface proteins | 9/10 |
| E | 11 | γ hemolysin B and C subunit | 1 |
| F | 1 | Novel exotoxin (exotoxin 2 like) | 8 |
| F | 2 | Novel exotoxin (exotoxin 2 like) | 8 |
| F | 3 | Novel exotoxin (exotoxin 2 like) | 8 |
| F | 4 | Novel exotoxin (exotoxin 2 like) | 8 |
| F | 5 | Novel hemolysin (YjfD) | 11 |

What is claimed is:

1. An immunogenic composition comprising a carrier or adjuvant and at least one isolated polypeptide comprising the amino acid sequence of SEQ ID NO.: 27.

2. The immunogenic composition of claim 1, wherein said isolated polypeptide comprising the amino acid sequence of SEQ ID NO. 27 is a recombinant polypeptide.

3. The immunogenic composition of claim 1, further comprising an isolated polypeptide comprising the amino acid sequence of SEQ ID NO. 28.

4. The immunogenic composition of claim 1, further comprising an isolated polypeptide comprising all or a portion of SEQ ID NO. 29.

5. The immunogenic composition of claim 1, wherein said immunogenic composition is formulated for administration to a subject, wherein said administration is selected from the group consisting of intravenous injection, intramuscular injection, subcutaneous injection and orally.

6. The immunogenic composition of claim 1, further comprising at least one protein from *Staphylococcus aureus*.

7. The immunogenic composition of claim 1, wherein said immunogenic composition is capable of generating an effective immune response against *Staphylococcus aureus*.

* * * * *

SEQUENCE LISTING

<160> NUMBER OF SEQ ID NOS: 32

<210> SEQ ID NO 1
<211> LENGTH: 2260
<212> TYPE: DNA
<213> ORGANISM: Staphylococcus aureus

<400> SEQUENCE: 1

```
gatcttaatg aaagagtgac tgatgcctta gcaattgcta gttgtatcaa tgcgcatccg      60
tatgtcaaag gagaactttg cgtgtccgat gacttaacgt atacgacagg ttattttgcc     120
gctgctaaaa ttggttacca tcgattattt gatattaaac cagttaatac gagatatgga     180
ggcagaataa tatttgtgga cgattgtatt gatttaaatc attacatatc attttttagaa    240 agcacaccga agcaagttgt ttatgaaacg gtataggggg tttagtatga catcaaaaga     300
tattactcaa attagtgtca ttgctgcgat tttaaccatt ttggcagttt tgaaaatacc     360
gtccattata ccaggattag attttcaatt atctgcaccg gcagcattat tgatattagc     420
tttctttgga attaaaaagt acttttttagg tggattatta tctagcctat tattactagt     480
atttggcgta tttaatccaa ttaatgtgat tatctctatt atatttagag ttatagctat     540
tgcagttgtt tatttattga aaataaatgt actatcatta gttttagcaa gtgtattagg     600 cagttttggta tataggctac tattatctat tattttaaat ttacctgtgt gggtagtgtt     660
gttaaacgcg attccaggcg taatattcac tttaattgta gctattcctt tatatctcac     720
attgagaaaa agaatggcag tattactaag ataataaatc aaaacacggt cgtcacaatt     780
actgttggcg accgtgtttt actagctatt tattgttttc agtttctttt gtatctaaca     840
atttcacttt gtgattttcc caatcaattt catatgttga tttaaatgtt ctagttttaa     900 agttttata atttgcgcct gcccagtaga agccattcca acgaatttgg tataaatcca     960
tttcacgttg ataagttact gtaattttag attttttagc gccatcttgt ctgtgtgata    1020
gtacgcttaa aaattctgga ttgaagttac ttctagataa taatggcatt tggtgttgcg    1080
ctatgaagtt ttggccagcg tatgcactgc tttgtctgcc agctaagaag agttcattac    1140
catatgttgg gtggaagcta tctcttccat aaggtcccca accattattc ataattttat    1200
gtgcttcaac tccccagcca acatttttat aatttgtgtt gcgacttaat gttgttctgt    1260
aactttcttg tttataatta attgtttcag aaaaagctgt atttccatta agtccaccag    1320
ataaaccatt agagatacta atgtcaccac caaatgtata gcctaaagta ttttgaactt    1380
gaaactcttc atttttgattt tttggtgcat aatcaacgac gtttactgaa tcattagatt    1440
gtgagcttat agatacattg tatttagctc cccaatataa ttttgaaaag tcatagtcat    1500
taggattagg tttcacaaag cctgagttaa tattcccagt agctttaagt actaaagtat    1560
```

| | |
|---|---|
| ctttatcata actttttatct ttgatgaaat taaatgttaa aatctgtgaa attttaaatt | 1620 |
| tatcagaatc tgctgtggct gttgttttgt ataaagtaac tttgtcatcg acttttttta | 1680 |
| cgctgactgg tgttatttta ccttcagcat tagcagtacc agaaagtaat aataatgcca | 1740 |
| tagatgtagc aacggatgat ttgactaatt tattcatttt catatcaatt ctgtcctttc | 1800 |
| accttgattt catgagtctt ccaattgacc tcgtatttca cagtatagtt tctatttaca | 1860 |
| aatgcattat ggactctatg tccgtctaaa taactgttgc cataatgcgt tgatctttta | 1920 |
| atggcatgag tgacatccat gtttcttccg taagtaattt caaattcgct tgtatcgctt | 1980 |
| gaacctttt catgagatac tgtggcgata aatgaagggt taaatccact ttgtacaaga | 2040 |
| ggtggtaact cactgtctgg aacgaaataa tctctaggat ctttactatg aggtttgtag | 2100 |
| cctacaaata aatcgctatc aaaggctgat ttttgacctg attcagtggc gaatgaattc | 2160 |
| gctttgacgc cccataaaac acttttttgag ttttgttgtt ctacttcact tacataattt | 2220 |
| tgttgtgtat agctaatcga tttagaatag ttaaatgatc | 2260 |

<210> SEQ ID NO 2
<211> LENGTH: 2902
<212> TYPE: DNA
<213> ORGANISM: Staphylococcus aureus

<400> SEQUENCE: 2

| | |
|---|---|
| gatcgtataa tcgaaacagc accaacggat tacttatctt ggggtgtcgg tgcagtcggt | 60 |
| aaccctagat tcatcaatgt tgaaatcgta cacacacacg actatgcttc atttgcacgt | 120 |
| tcaatgaata actatgctga ctatgcagct acacaattac aatattatgg tttaaaacca | 180 |
| gacagtgctg agtatgatgg aaatggtaca gtatggactc actacgctgt aagtaaatat | 240 |
| ttaggtggta ctgaccatgc cgatccacat ggatatttaa gaagtcataa ttatagttat | 300 |
| gatcaattat atgacttaat taatgaaaaa tatttaataa aatgggtaa agtggcgcca | 360 |
| tggggtacgc aatctacaac taccccctact acaccatcaa aaccaacaac accgtcgaaa | 420 |
| ccatcaactg gtaaattaac agttgctgca acaatggtg tcgcacaaat caaaccaaca | 480 |
| aatagtggtt tatatactac tgtatacgac aaaactggta aagcaactaa tgaagttcaa | 540 |
| aaaacatttg ctgtatctaa aacagctaca ttaggtaatc aaaaattcta tcttgttcaa | 600 |
| gattacaatt ctggtaataa atttggttgg gttaaagaag gcgatgtggt ttacaacaca | 660 |
| gctaaatcac ctgtaaatgt aaatcaatca tattcaatca aacctggtac gaaactttat | 720 |
| acagtacctt ggggtacatc taaacaagtt gctggtagtg tgtctggctc tggaaaccaa | 780 |
| acatttaagg cttcaaagca acaacaaatt gataaatcaa tttatttata tggctctgtg | 840 |
| aatggtaaat ctggttgggt aagtaaagca tatttagttg atactgctaa acctacgcct | 900 |
| acaccaacac ctaagccatc aacacctaca acaaataata aattaacagt ttcatcatta | 960 |
| aacggtgttg ctcaaattaa tgctaaaaac aatggcttat tcactacagt ttatgacaaa | 1020 |
| actggtaagc caacgaaaga agttcaaaaa acatttgctg taacaaaaga agcaagttta | 1080 |
| ggtggaaaca aattctactt agttaaagat tacaatagtc aacttttaat tggttgggtt | 1140 |
| aaacaaggtg acgttattta taacaatgca aaatcacctg taaatgtaat gcaaacatat | 1200 |
| acagtaaaaac aggcactaa attatattca gtaccttggg gcacttataa acaagaagct | 1260 |
| ggtgcagttt ctggtacagg taaccaaact tttaaagcga ctaagcaaca acaaattgat | 1320 |
| aaatctatct atttatttgg aactgtaaat ggtaaatctg ttgggtaag taaagcatat | 1380 |
| ttagctgtac ctgctgcacc taaaaaagca gtagcacaac caaaaacagc tgtaaaagct | 1440 |

-continued

```
tatactgtta ctaaaccaca aacgactcaa acagttagca agattgctca agttaaacca    1500
aacaacactg gtattcgtgc ttctgtttat gaaaaaacag cgaaaaacgg tgcgaaatat    1560
gcagaccgta cgttctatgt aacaaaagag cgtgctcatg gtaatgaaac gtatgtatta    1620
ttaaacaata caagccataa catcccatta ggttggttca atgtaaaaga cttaaatgtt    1680
caaaacttag gcaaagaagt taaaacgact caaaaatata ctgttaataa atcaaataac    1740
ggcttatcaa tggttccttg gggtactaaa aaccaagtca ttttaacagg caataacatt    1800
gctcaaggta catttaatgc aacgaaacaa gtatctgtag caaagatgt ttatttatac     1860 ggtactatta ataaccgcac tggttgggta aatgcaaaag atttaactgc accaactgct    1920
gtgaaaccaa ctcatcagc tgccaaagat tataactaca cttatgtaat taaaaatggt     1980
aatggttatt actatgtaac accaaattct gatacagcta aatactcatt aaaagcattt    2040
aatgaacaac cattcgcagt tgttaaagaa caagtcatta atggacaaac ttggtactat    2100
ggtaaattat ctaacggtaa attagcatgg attaaatcaa ctgatttagc taagaattga   2160
attaagtata atcaaacagg tatggcatta accaagttg ctcaaataca agctggttta    2220
caatataaac cacaagtaca acgtgtacca ggtaagtgga caggtgctaa ctttaatgat    2280
gttaagcatg caatggatac gaagcgttta gctcaagatc cagcattaaa atatcaattc   2340
ttacgcttag accaaccaca aaatatttct attgataaaa ttaatcaatt cttaaaaggt    2400
aaaggtgtat tagaaaacca aggtgctgca tttaacaaag ctgctcaaat gtatggcatt    2460
aatgaagttt atcttatctc acatgcccta ttagaaacag gtaacggtac ttctcaatta    2520
gcgaaaggtg cagatgtagt gaacaacaaa gttgtaacta actcaaacac gaaataccat    2580
aacgtatttg gtattgctgc atatgataac gatcctttac gtgaaggtat taaatatgct    2640
aaacaagctg gttgggacac agtatcaaaa gcaatcgttg gtggtgctaa attcatcggc    2700
aactcatatg taaaagctgg tcaaaataca ctttacaaaa tgagatggaa tcctgcacat    2760
ccaggaacac accaatatgc tacagatgta gattgggcta acatcaatgc taaaatcatc    2820
aaaggctact atgataaaat tggcgaagtc ggcaaatact tcgacatccc acaatataaa    2880
taagcaacat gaacatagga tc                                              2902
```

<210> SEQ ID NO 3
<211> LENGTH: 2792
<212> TYPE: DNA
<213> ORGANISM: Staphylococcus aureus

<400> SEQUENCE: 3

```
gatcaactta atataatgaa ttcggcaaca gaagagcatc atcataaaga ttatattaaa      60
ctatataatt taggtggcgg tgctgctaaa aaaattgcaa tagaggtttt attggggaag    120
gataaagtca ttcagaaaaa atacgtgcat atttttaccta gtaaagaagg gtacatgtta    180
ccaattaata aaaatgtgta cgaagaatta gaaagaacga ttgagaacaa tggtcatgaa    240
gctgatttga atgtacgtat gacttattat cataatgtaa gtcgcaaaca acaggaagtt    300
atattaaaag gtcaaatcga ccgttttaat acttataata taaagaaat ttatgatttg      360 cagtttatct aaaaattgat ttaagagggt agttgtttat tgcgaaaaat atcattcaat    420
tttaatgaaa taatggcgtc attactataa aatattactt tatgttgtaa tgcattttc     480 tataagatag aactaaaagg agggggcaaag atgcaaatta gacaaataca tcaacatgac    540
tttgctcaag tggaccagtt aattagaacg gcatttgaaa atagtgaaca tggttatggt    600
aatgaatcag agctagtaga ccaaattcgt ctaagtgata cgtatgacaa taccttagaa    660
```

```
ttagtagctg ttcttcaaaa tgaagttgta gggcacggtt tactaagtga agtttatctt    720
gataacgagg cacaacggga aattggatta gtgttagcac ctgtatctgt tgatattcat    780
catcaaaata aggtattgg gaagcgattg attcaagcat tagaacgaga agcaatatta    840
aaaggatata attttatcag tgtattagga tggccgacgt attatgccaa tctaggatat    900
caacgcgcaa gtatgtacga catttatcca ccatatgatg gtataccaga cgaagcgttt    960
ttaattaaag aattaaaagt gaacagttta gcgggaaaaa caggtaccat aaattacaca   1020
tctgcttttg aaaaaatatg atttcaagct aggattacat taggtagagt tcatattaat   1080
aataaaaaat gtttgcaatc aaatcgtacg ttgtcgtttg taattcttaa aatagcaata   1140
aataaaatgt ttgttagtaa agtattattg tggataataa aatatcgata caaattaatt   1200
gctataatgc aattttagtg tataattcca ttaacagaga ttaaatatat ctttaaaggg   1260
tatatagtta atataaaatg acttttttaaa aagagggaat aaaatgaata tgaagaaaaa   1320
agaaaaacac gcaattcgga aaaaatcgat tggcgtggct tcagtgcttg taggtacgtt   1380
aatcggtttt ggactactca gcagtaaaga agcagatgca agtgaaaata gtgttacgca   1440
atctgatagc gcaagtaacg aaagcaaaag taatgattca agtagcgtta gtgctgcacc   1500
taaaacagac gacacaaacg tgagtgatac taaaacatcg tcaaacacta ataatggcga   1560
aacgagtgtg gcgcaaaatc cagcacaaca ggaaacgaca caatcatcat caacaaatgc   1620
aactacggaa gaaacgccgg taactggtga agctactact acgacaacga atcaagctaa   1680
tacaccggca acaactcaat caagcaatac aaatgcggag gaattagtga atcaaacaag   1740
taatgaaacg acttctaatg atactaatac agtatcatct gtaaattcac ctcaaaattc   1800
tacaaatgcg gaaaatgttt caacaacgca agatacttca actgaagcaa caccttcaaa   1860
caatgaatca gctccacaga gtacagatgc aagtaataaa gatgtagtta atcaagcggt   1920
taatacaagt gcgcctagaa tgagagcatt tagtttagcg gcagtagctg cagatgcacc   1980
ggcagctggc acagatatta cgaatcagtt gacgaatgtg acagttggta ttgactctgg   2040
tacgactgtg tatccgcacc aagcaggtta tgtcaaactg aattatggtt tttcagtgcc   2100
taattctgct gttaaaggtg acacattcaa aataactgta cctaaagaat aaacttaaa   2160
tggtgtaact tcaactgcta aagtgccacc aattatggct ggagatcaag tattggcaaa   2220
tggtgtaatc gatagtgatg gtaatgttat ttatacattt acagactatg taaatactaa   2280
agatgatgta aaagcaactt tgaccatgcc cgcttatatt gaccctgaaa atgttaaaaa   2340
gacaggtaat gtgacattgg ctactggcat aggtagtaca acagcaaaca aaacagtatt   2400
agtagattat gaaaaatatg gtaagtttta taacttatct attaaaggta caattgacca   2460
aatcgataaa acaaataata cgtatcgtca gacaatttat gtcaatccaa gtggagataa   2520
cgttattgcg ccggttttaa caggtaattt aaaaccaaat acggatagta atgcattaat   2580
agatcagcaa aatacaagta ttaaagtata taagtagat aatgcagctg atttatctga   2640
aagttacttt gtgaatccag aaaactttga ggatgtcact aatagtgtga atattacatt   2700
cccaaatcca aatcaatata agtagagtt taatacgcct gatgatcaaa ttacaacacc   2760
gtatatagta gttgttaatg gtcatattga tc                                2792
```

<210> SEQ ID NO 4
<211> LENGTH: 2478
<212> TYPE: DNA
<213> ORGANISM: Staphylococcus aureus

<400> SEQUENCE: 4

-continued

```
gatcgaattg aacgaagcat ttgcttctca aacgattgca tctattaaag aagtaggtct      60
agatatatca cgtacgaatg tgaatggtgg cgctattgct ttaggtcatc cattaggtgc     120
tacaggcgca atgttaaccg cgcgtttact taatgaaatg ggtagacgtc ccgatagccg     180
ttacggcatg gttacgatgt gtattggtgt cggcatgggt gcagctgcta tatttgaata     240
tgtgcgttag aatggttgat tttggatgaa gcggattcgt tttgttattg aatgaagtag     300
gctgaagttg aagccagttg aagttgaagc gggttgaagc aatttcgttt tattaatgaa     360
gctgtgtgaa atatagtgat tgaacaaaaa agtggtttaa tgggatggtg gttatttccg     420
ttttagaatt taacatttac acgtctaatt ttaatcattg ttttaaattt tatgaatcga     480
agccctttga tttaataata tttgctaatg ctagtaactt atctgattgt tcatgtttaa     540
aataaagaaa accactcaca tcagtgtgtg ttcgaactag acttgtaagt tccagttcgg     600
cacgactttc taaagcaatt attattgctg tgattgtcgt atatcactta gatgtgcgtg     660
gtttatttta ataggttagt aatatattag gtcatgttat gtttaagact ataatgaata     720
aataatttag aaatatgctt ccgattgttc gatgctttaa ttcagttaga agcatcatag     780
aatgcatgat tactgttgta aagatacgta atgttttgta ttgactgtat gtctttggat     840
agagttacaa acttatttg ttactctagg cccatatgtc gcagtaccat ctgcatgtgt      900
tgttacattg tatgcatttg ttttacttgg cttcttgtat gtcgggcgag ctccgtatga     960
cacttgaccg tttgcatgtg ttgttacgtt gtatgcattt gttttgcttg cttgttttg    1020 tgttgggcga gcgccatatg atacttggcc gtttccatgt gttgttacgt tatatgcgtt    1080
tgttttgctt ggcttgtttt gtgtcggacg agctccgtat gatacttggc cgtttgcatg    1140
tgttgttaca ttgtatgcat tcgtttcgct tggcttcttg tatgtcggac gagctccgta    1200
tgatacttga ccatttgcat gtgttgttac gttatatgca tttgtttctg atggcttatt    1260
gaatcttggt ctcgcttcat atccaaatgt tccatcgttg tattcacgga tacctgtacc    1320
agcatctcta tatttaacat atttaggtgt tttgttaaat tgcggtctcg gaccatattg    1380
agaagcttct gttgtttcag ttgcttgagg tttaacttca atatcacttg attctccttg    1440
agtacctttt aacgttgatt cagtaccttg tggttttatt tcaagtttag atgagctacc    1500
ttcaagacct tctaaaatag ggttcgttaa cggtgggttt gtataattat tgcttaatga    1560
tgggccgctt tgttccattg ttagaaaatc gggaccttga acgatttcac cttgtaccgt    1620
tttattttcc atcgttggat attccggacc ttttacaatt tcacctgtaa ttgtgccctg    1680 tggaattta actaatggtt gtgcaactgg ttgtgttgtt tcttcagctt taccagccgt     1740
agttttaacc tcttgttggt tatcaacttt aggtgcttga ggttcttcaa ctttcttctc    1800
ttcttttact actggcgatt ttgtttcagt ttctccgtat tttttgacag ttttcttttt    1860
ccaagaatca tctgcttctt taactgcttt tttcgtttct tcaactaatt tatcaaaatt    1920
aggtttatta tcactatttg ttttatagtt atgtgttgta ggattatatt tcgttataga    1980
tttcggtcta ttttgtttag tttccataaa gaaatcatca ataattgaat ttaagtcatc    2040
aatcatttct tttttaatac gttcatttgt aattttatgt ggattgtctg tatctccaag    2100
gattaagtcc agttttgctc gtaactcttt cgcgtgctcc ccataatcct tatcaccata    2160
atatgataca actaatgtat caatttcaga tacgagatcg tatacttcct tagttgcttt    2220
atcttcttct gctgcattaa aagttttcaa gtctgaattc ttatccttaa tatctttaac    2280
ttctctgtga aaatcatcca gtgctctctt taatgcatcc tgtagttcat tgtattcttt    2340
catcgaaagt tcttctaaat tatatttatg aaaattagcc attttttaaat ctgtacgagg    2400
```

| | |
|---|---|
| attttcttt ttataatttg cataccattg tttataatct tcatattgag atttctttct | 2460 |
| ctccaaaaga tattgatc | 2478 |

<210> SEQ ID NO 5
<211> LENGTH: 2070
<212> TYPE: DNA
<213> ORGANISM: Staphylococcus aureus

<400> SEQUENCE: 5

| | |
|---|---|
| tgacgctgct tttgtaaata catataattt ttccacttca tgatttaatt cgttcgcatg | 60 |
| atctttgtaa tttctaccaa aagcaatcac attattcgga ggtgttactg gtggtaaaaa | 120 |
| ttcaatgtca ttaaatgaaa ttttatagtc ttcagctttg ccgctatctt ctgctgctac | 180 |
| aactgcttta cgtacttgtt cttgaaaatc taaagtatga ttttgttgta aaccagctaa | 240 |
| caatgtttta ggatggaaat ctccttctgc aaagtcagca atacttgtg ttaaatccca | 300 |
| tacagcatct tcgcgtttta ctttaacgcc atatgaagtt tgtcattat acttgaatga | 360 |
| taagaatttc attcattctc aactcctcgt ctttatctta attcacatta taactttttt | 420 |
| cgttatcaaa taacaaataa ataagtaaga caattttgaa aatgagttgt gttcattctg | 480 |
| ctacaaggac tttgcactta atcgaaatta ttttttattc ttttgaaaat caaatacta | 540 |
| tagttgcaat gtaccaaatt tgaagaagta taaataacct ttaacttctt tattaagaat | 600 |
| cgtttgaagc gtattttgat aatatttcat ctgtatctta tatttatttt ttaattgtgt | 660 |
| accaatttct tcatctgtca tcccacggcg acgattaaat gcatcggttt tatagtctac | 720 |
| aaaataatgc acaccatctt taacaaagat taagtcaatc ataccttgaa taattgagac | 780 |
| gtcttcgtct cctgtggca attggtcaac taatgcttgg ttaactacaa acggtaattc | 840 |
| acgataaact tgctctgctt cagcaataat cgaatataac tcactattga taaatgtcat | 900 |
| tatttcatcc atacggatat cttttttcgc atctgcttcg ataatatgtt tatcgattaa | 960 |
| tccatcgata tactgatgta actcaacttc agatatgcgt tcttttttga atggtaaatg | 1020 |
| ttgcatcact gtatgcatta acgtaccaat ttcattcgct tttcgtttac cttgttcact | 1080 |
| tagaaattta ggtcgttcat acgttgaaaa accgatacga tattgcctta ctcgttcgta | 1140 |
| acttgtgcca cttcttctg tttcatattg tcttttcaat tcagaaacag attgttttga | 1200 |
| gggcttttta gtatcattta catatggata tcgataatca agttggtgtt taatttgtgc | 1260 |
| tttaacatct tcattaccat tttgcatagt ttctaattga ttaaccgaac gatattcatc | 1320 |
| attatctaaa atggtttctg tagacacatc ttcaaagtac acaattgaaa tatttacatt | 1380 |
| cggacgacta ctatcttcaa tttgtgctat atcttttca aattttaaat catctggaat | 1440 |
| tgacgcagat tgatgtttag ataaaatact ataaataaga tggaacggat ttggtgaagt | 1500 |
| taatcgttca ttgacagcaa tgtgctcacc agaaatagac aattgctcta gttctagtaa | 1560 |
| tgatttatca tttttcactc taccaattaa ataagttgt tctttcgctc ttgttaatgc | 1620 |
| tacatagact aatcgcattt cttctgacac aagttctttt tcggcaacag ctctatatgc | 1680 |
| aaccgaagct aaagatggaa atgccatttc tttatccaca tcaaaataat ccattccgag | 1740 |
| accaaattgc tgatttaaaa taactggttg tttcaaatca cgttattaa aatcttttga | 1800 |
| caatccagaa taaatgacaa atggaaactc tagaccttta ctactatgaa ttgtcatcat | 1860 |
| tctaacgaca ttatcgtttg gaccaactac attttcctca ccaaaatctt tgcctctttc | 1920 |
| aatcaattca tcgataaaac gaataaattg atataaacct ctaaaacttg aattctcaaa | 1980 |
| ctcgatagct ttattaaata aaccataaag atttgcacgt cgtccacgtc caccaataag | 2040 | tccactaaag tattgaataa cataatgatc        2070

<210> SEQ ID NO 6
<211> LENGTH: 2394
<212> TYPE: DNA
<213> ORGANISM: Staphylococcus aureus

<400> SEQUENCE: 6

| | | |
|---|---|---|
| gatcagattt attagacagt attccagata tacccacacc aaagccagaa aagacgttaa | 60 |
| cacttggtaa aggtaatgga ttgttaagtg gattattaaa tgctgatggt aatgtatctt | 120 |
| tgcctaaagc gggggaaacg ataaaagaac attggttgcc gatatctgta attgttggtg | 180 |
| caatgggtgt actaatgatt tggttatcac gacgcaataa gttgaaaaat aaagcataat | 240 |
| tatattgggg gaagagcatc tatatatttt tttaagtata taagacgtct tatttcccct | 300 |
| taatttattg tgaagtatat gcaaaatgca atgaatagat tgtccatcat tttaacgtta | 360 |
| taatgaattt aacgacttag aactacacaa gtaaggaga atgaagatgt ctcgaaaaac | 420 |
| ggcgctatta gttttggata tgcaagaagg tatagcgagt agtgtaccta gaataaaaaa | 480 |
| tattattaaa gcgaatcaga gagcaattga agcagcaaga caacatcgaa taccagtcat | 540 |
| tttcatacgt ttagtgttag ataagcattt taatgatgtc tcctcgagta taaagtgtt | 600 |
| ttcaacaatt aaagctcaag gatatgcgat tactgaagca gatgcatcta cacgaatact | 660 |
| tgaagattta gcaccactag aagatgagcc gattatttct aagcgacgct ttagcgcatt | 720 |
| tacaggtagt tacttggaag tttatttacg tgcaaatgat attaatcatt tagtattaac | 780 |
| gggtgtctct acaagtggag ctgtattgag cacggcatta gaaagtgtag ataaagacta | 840 |
| ttatattact gttttagaag atgctgttgg tgatagatca gatgataaac atgactttat | 900 |
| tattgaacaa attttatcac gctcatgtga cattgaatcc gtagagtcat ggaaaagtag | 960 |
| tttatagtta atataacgtc aattaaagct cggcagtaat gtttgagaat aagtacattt | 1020 |
| gctcatattt ataaaatgtg tgagatggca attgaaacgg atatgatgag gaacatttga | 1080 |
| acataaaata atatatttat ataaaacgac ccgaggcgtt cgaactgaat gcctcgggtt | 1140 |
| taattgaata agaaatcgga cttatgaaca gaaatatgtt taagtccgaa ctccttgttt | 1200 |
| atacttataa attttacggg tttaatataa tacttattta cctgtaatat atgataattc | 1260 |
| ttcagcggca gctgcgttga tagttctatg agaaatgata cctaatcctt taacattgga | 1320 |
| ttctgaaata acgatagaac catcactgtt aactttttca acaaatgcta catgaccgta | 1380 |
| atgttgatct gcaccaaatt gtccagcctc aaatacaaca gcagcatgac gttttggtgt | 1440 |
| atgacttact tgataatcac ggtattgagc tcgattattc caattatgtg catcaccctaa | 1500 |
| atcacctgag atagatgtac caaattgttt catacggtta tatacgtacc aagtacattg | 1560 |
| gccatgtgga tatggcatac tatcagatac ctcacggaaa ggtttgaatt catctgatga | 1620 |
| atcatcataa tccttgatag aacgttcata tttatctaaa tctggcatgc gttcatcgtc | 1680 |
| aaactgagtt aattgatagt gtttaataat actgtttaat ttcttagcat agtttggatc | 1740 |
| tgtagcatat gttttagata agtgtgatgt tgcatcttta taagaatcgg cttccgattt | 1800 |
| ccatgttggt ttataaattg ttcgattgcc atcaatacca ttttttaataa ggtcagagta | 1860 |
| atcttttagt gattctttcg tgcttggata ttttcggaat ccagcattaa tactatacaa | 1920 |
| ttgattacca tcagcttcta atgtgttaaa aggaacagaa ttcccttcaa aagcaccttt | 1980 |
| gataccgaat aaattatggt ttggtgactt agctaaagca ctcgacctg agtcagattc | 2040 |
| taagattgct tgggcaatca tgacagacgc ataaatatcg ttatcttgac caatgcgatg | 2100 |

| tgcatcttta gcaattgatt tgacaaattg acgtgtatct tttgagtcaa caacgttaaa | 2160 |
| ttgtccgcta tcatcattgt tagatatact aggatctgtt tcgaataatg atgttgcacg | 2220 |
| tgtatccttt tgattaacat cgttattgaa tgattgagca ggtttagatt tatgtttcaa | 2280 |
| ttcatcttgt gttggtaact gtggattctt tgtattagat ttttcatttt tgtcttttt | 2340 |
| agattgagat gcataatctt tttgtgtttt ctttgcatct tcactgtatt gatc | 2394 |

<210> SEQ ID NO 7
<211> LENGTH: 2033
<212> TYPE: DNA
<213> ORGANISM: Staphylococcus aureus

<400> SEQUENCE: 7

| gatctggaac aggtttcatt gtcggtaaaa atacaattgt taccaacaag catgtcgttg | 60 |
| caggtatgga aattggtgca catattatag cgcatcccaa tggtgaatat aataatggcg | 120 |
| gattttataa agttaaaaaa attgtccgtt attcaggtca agaagatatt gccattctac | 180 |
| atgtggaaga taaagctgtt catccaaaaa acaggaattt taaagattac acaggcattt | 240 |
| taaaaatagc atcagaagct aaagaaaatg aacgcatttc aattgttggc tatccagaac | 300 |
| catatataaa taaatttcaa atgtatgagt caacaggaaa agtgctgtca gttaaaggca | 360 |
| acatgattat tactgatgct ttcgtagaac caggcaactc aggttcagct gtatttaaca | 420 |
| gtaaatacga agttgtaggt gttcactttg gtggaaacgg ccctggaaat aaaagtacaa | 480 |
| aaggatatgg tgtttatttc tctcctgaaa ttaagaaatt cattgcagat aacacagata | 540 |
| aataaatcct tacatagata aatgatttta aaaattaaca acaaactcaa caattcaaat | 600 |
| catctctgtg attccattta ttcgaaatga ttaaaaaaaa taaacttca aaaagctaac | 660 |
| attataatta tacaaatact tagaggagca gaaaaatgaa taaaaatata atcatcaaaa | 720 |
| gtattgcagc attgacgatt ttaacatcaa taactggtgt cggcacaaca atggttgaag | 780 |
| gtattcaaca aacagccaaa gccgaaaata ctgttaaaca aattacaaat acaaatgttg | 840 |
| caccatacag tggtgttaca tggatgggcg ctggaacagg atttgtagtt ggaaatcata | 900 |
| caatcattac caataaacat gttacctatc acatgaaagt cggtgatgaa atcaaagcac | 960 |
| atcctaatgg ttttttataat aacggtggtg gactttataa agttactaag attgtagatt | 1020 |
| atcctggtaa agaagatatt gcggttgtac aagttgaaga aaaatcaaca caaccaaaag | 1080 |
| gtagaaaatt caaagatttc actagtaaat ttaatatagc atcagaagct aaagaaaatg | 1140 |
| aacctatatc agtcattggt tatccaaatc ctaatggaaa taaactacaa atgtatgaat | 1200 |
| caactggtaa agtattatca gtgaatggga atatagtgtc ttcggatgca attattcagc | 1260 |
| ctggtagctc tggttcacct atattaaata gtaaacacga agctattggt gtaatctatg | 1320 |
| ccggtaataa gccatcaggt gaaagcacaa gaggatttgc tgtttatttc tctcctgaaa | 1380 |
| ttaagaaatt cattgcagat aatttagata ataattaaa acttagacat tcacccaatc | 1440 |
| ctgacaaaat atactataac taacatttat taatatatat tgcattattt aatatgcatc | 1500 |
| aaagccaatc aacgattgat tttcaccaac tcaattgttg attggtttta tttatgtatg | 1560 |
| aatgaacaac tttttgacat cattaagaat ataaatgatt ttgaaagcat tgaaagcta | 1620 |
| caacatttct ataaaatttt tcaataacaa ttgcgccact aaaactcaaa atttccacca | 1680 |
| ccaacatcca aattatcaac atcgcaacat aaccaaatgt tataataaat ctattacaca | 1740 |
| aagagataaa ttacttatgc aaaggcggag gaatcacatg tctattactg aaaaacaacg | 1800 |
| tcagcaacaa gctgaattac ataaaaaatt atggtcgatt gcgaatgatt taagagggaa | 1860 |

```
catggatgcg agtgaattcc gtaattacat tttaggcttg attttctatc gcttcttatc    1920
tgaaaaagcc gaacaagaat atgcagatgc cttgtcaggt gaagacatca cgtatcaaga    1980
agcatgggca gatgaagaat atcgtgaaga cttaaaagca gaattaattg atc           2033

<210> SEQ ID NO 8
<211> LENGTH: 2794
<212> TYPE: DNA
<213> ORGANISM: Staphylococcus aureus

<400> SEQUENCE: 8
gatcaaacgt tgcttaactt cttttaatg cttaaaaatt atttcaaagg cacatagaaa      60
cgctatatta atctcatact cactcattat tttttgctta aattacttaa taatacttca    120
ataattgtta aaggggtttt aatgtgatta tcttagaacg ccatctataa tgatgttgta    180
tgattcaaat tacgtaaaaa gacaatcgaa tataatatag attggagcat acaattatga    240
aaatgagaac aattgctaaa accagtttag cactagggct tttaacaaca ggcgcaatta    300
cagtaacgac gcaatcggtc aaagcagaaa aaatacaatc aactaaagtt gacaaagtac    360
caacgcttaa agcagagcga ttagcaatga taaacataac agcaggtgca aattcagcga    420
caacacaagc agctaacaca agacaagaac gcacgcctaa actcgaaaag gcaccaaata    480
ctaatgagga aaaaacctca gcttccaaaa tagaaaaaat atcacaacct aaacaagaag    540
agcagaaaac gcttaatata tcagcaacgc cagcgcctaa acaagaacaa tcacaaacga    600
caaccgaatc cacaacgccg aaaactaaag tgacaacacc tccatcaaca aacacgccac    660
aaccaatgca atctactaaa tcagacacac cacaatctcc aaccataaaa caagcacaaa    720
cagatatgac tcctaaatat gaagatttaa gagcgtatta tacaaaaccg agttttgaat    780
ttgaaaagca gtttggattt atgctcaaac catggacgac ggttaggttt atgaatgtta    840
ttccaaatag gttcatctat aaaatagctt tagttggaaa agatgagaaa aaatataaag    900 atggaccttta cgataatatc gatgtatttta tcgttttaga agacaataaa tatcaattga    960
aaaaatattc tgtcggtggc atcacgaaga ctaatagtaa aaaagttaat cacaaagtag   1020
aattaagcat tactaaaaaa gataatcaag gtatgatttc acgcgatgtt tcagaataca   1080
tgattactaa ggaagagatt tccttgaaag agcttgattt taaattgaga aaacaactta   1140
ttgaaaaaca taatctttac ggtaacatgg gttcaggaac aatcgttatt aaaatgaaaa   1200
acggtgggaa atatacgttt gaattacaca aaaaactgca agagcatcgt atggcagacg   1260
tcatagatgg cactaatatt gataacattg aagtgaatat aaaataatca tgacattctc   1320
taaatagaag ctgtcatcgg aaaaacaaga agttaagtga caacggttta catgttgctt   1380
agcttctttt attatgcgta atgatgtaaa aagacgaata ttcatttgtt tgtaaaagtg   1440
gcatttctat gtcttaaaag tgacgaaact tcaaatgtgc caagtgttga atcacatcaa   1500
aatcattttt atttaacgaa cattatggat ttcttaattt acttaacgat gattcaaata   1560
tagttaaaca aggtttaatg tgaatggagc aatacgccat ctataataaa gctgtatgat   1620
tcaatgaatg taatcgaaca aatctaataa ttacgaatgg agcatacaac tatgaaaata   1680
acaacgattg ctaaaacaag tttagcacta ggccttttaa caacaggtgt aatcacaacg   1740
acaacgcaag cagcaaacgc gacaacacta tcttccacta agtggaagc accacaatca   1800 acaccgccct caactaaaat agaagcaccg caatcaaaac caaacgcgac aacaccgccc   1860
tcaactaaag tagaagcacc gcaacaaaca gcaaatgcga caacaccgcc ttcaactaaa   1920
gtgacaacac ctccatcaac aaacacgcca caaccaatgc aatctactaa atcagacaca   1980
```

```
ccacaatcgc caaccacaaa acaagtacca acagaaataa atcctaaatt taaagattta      2040
agagcgtatt atacgaaacc aagtttagaa tttaaaaatg agattggtat tattttaaaa      2100
aaatggacga caataagatt tatgaatgtt gtcccagatt atttcatata taaaattgct      2160
ttagttggta aagatgataa aaaatatggt gaaggagtac ataggaatgt cgatgtattt      2220
gtcgttttag aagaaaataa ttacaatctg gaaaaatatt ctgtcggtgg tatcacaaag      2280
agtaatagta aaaagttgga tcacaaagca ggagtaagaa ttactaagga agataataaa      2340
ggtacaatct ctcatgatgt ttcagaattc aagattacta agaacagat ttccttgaaa       2400 gaacttgatt ttaaattgag aaaacaactt attgaaaaaa ataatctgta cggtaacgtt      2460
ggttcaggta aaattgttat taaaatgaaa acggtggaa agtacacgtt tgaattgcac       2520
aaaaaattac aagaaaatcg catggcagat gtcatagatg gcactaatat tgataacatt      2580
gaagtgaata taaataatc atgacattct ctaaatagaa gctgtcatcg gaaaaacaag       2640
aagttaagtg acaacggcct acatgttgct tagcttcttt tgttatgttc gatgatttga      2700
gaacccgaat tttcgatggg tccaaatatg acgtggaaga gacctgaatt tatctgtaaa      2760
tccctatcta tcgggtgtga agcacaacgg gatc                                 2794

<210> SEQ ID NO 9
<211> LENGTH: 505
<212> TYPE: DNA
<213> ORGANISM: Staphylococcus aureus

<400> SEQUENCE: 9
gatcatagcg caccaaactc tcgtccaatt gattttgaaa tgaaaagaa agatggaact        60 caacagtttt atcattatgc aagttctgtt aaacctgcta gagttatttt cactgattca      120
aaaccagaaa ttgaattagg attacaatca ggtcaatttt ggagaaaatt tgaagtttat      180
gaaggtgaca aaaagttgcc aattaaatta gtatcatacg atactgttaa agattatgct      240
tacattcgct tctctgtatc aaacggaaca aaagctgtta aaattgttag ttcaacacac      300
ttcaataaca agaagaaaa atacgattac acattaatgg aattcgcaca accaatttat      360
aacagtgcag ataaattcaa aactgaagaa gattataaag ctgaaaaatt attagcgcca      420
tataaaaaag cgaaaacact agaaagacaa gtttatgaat taaataaaat tcaagataaa      480
cttcctgaaa aattaaaggc tgagt                                           505

<210> SEQ ID NO 10
<211> LENGTH: 673
<212> TYPE: DNA
<213> ORGANISM: Staphylococcus aureus

<400> SEQUENCE: 10
gatcaaacta aaacacaaac tgctcataca gttaaaacag cacaaactgc tcaagaacaa       60
aataaagttc aaacacctgt taaagatgtt gcaacagcga atctgaaag caacaatcaa       120 gctgtaagtg ataataaatc acaacaaact aacaaagtta caaaacataa cgaaacgcct      180
aaacaagcat ctaaagctaa agaattacca aaaactggtt taacttcagt tgataacttt      240
attagcacag ttgccttcgc aacacttgcc cttttaggtt cattatcttt attactttc       300 aaaagaaaag aatctaaata aatcatcgtc acactcataa cttaatatat tttttatttt      360
aaatttattt taacctatgt catagatatt tcataatcta aacataggt tattttttt       420 ataaaataac gttgcaatta actaacattt caatgtcaat acaagtaatc aattgataat      480
gattatcagt tgataatata caattaggag ttgtttctac aacatgaaca aacagcaaaa      540
```
agaatttaaa tcattttatt caattagaaa gtcatcacta ggcgtgcatc tgtagcaatt    600
agtacacttt tattattaat gtcaaatggc gaagcacaag ccagcagctt gaagaaaaca    660
ggtggtccaa ttc                                                       673

<210> SEQ ID NO 11
<211> LENGTH: 2238
<212> TYPE: DNA
<213> ORGANISM: Staphylococcus aureus

<400> SEQUENCE: 11
gatcttcagc ttgatgtttt cgtttgatta aattggtaaa atagaaacgc aatccacaaa     60
aatggcaagc actaaaataa tgtttggggg tgcttgtgct tttgtggatt gcggtcgatt    120
atttatattg catgatttga ttaatttgat tgattatatt ggacatgatg gtgttggcgg    180
gatgcgttgt tgctagtcgc gggctttgtc cactccacat atgtattaac tctttgtcgc    240
cgatgtttgc tgcggctttt cttatgctac ttgttagctc attttgtatt ggataatctg    300
ggatatcgcc ttcgtattgg gacatttctt cgataaacct attgttgata ccgcgtgcaa    360
gctttccact aaacgctttt gtaatgactg tatctgtttc tttactattt ataattgcat    420
ctcgcagtag ttctgatgca ttactgtctt gtgatgttaa aaatgcggtg cccatttgta    480 cccttctgc acctaagaca atacttgcca aaactcctct accatccata attccaccag    540
cggcaatgac cggaattgaa acgacatcta caatttgtgg cactaaagat attgttccaa    600
ccataggtaa ttgatttta ggttttaaaa atgaaccacg atgtccacct gcttcactac    660
cttgagcaac gatagcatcc atacccgctt tttcattcgc aatagcttca tcaacacttg    720
ttgctgtacc tataagtttg acattcgctg ctttcaacct gcttataatc tgttcgcttg    780
gaattccaaa agtaaaacaa catacaggca cttgcttttt aattatcgta tcaatatgac    840 acttaaaattg ttgttcttcg gtaatttta caaccggctc ttctaaatgt aatgcgcgtc    900
gataaggttt taaccatgca ttcatatttt caatttgact actggtatat gattgttgac    960
ttggtacaaa gacatttacg ccaaaagaat ttgacgttaa ttggcgtaca taatctattt   1020
catcttccaa ttgctgcgta ttaaagtaac ctgcgcctat tgtgcctaac ccaccactgt   1080
tacttactga tgcaactaat ttcggtgtcg tacttcctgc catacctgct tgtataattg   1140
gatattcaat acttaacatt tgagtaagtc gattcttatt ccacatagct gttcgctcct   1200
tatatagata cgttgcgatt tttccgttgt tgaaattgaa tttgctgttg agaaagtttt   1260 tcttttcct ttttatccat ctcatcttca atttccatac ctaataattc ttcaattaag   1320
tcttcatgtg acactatcgc ttcagtacca ccaaattcgt ccaacacaat tgctaaatgt   1380
tttctagaaa tagtcatctt acgtaatacc cattcagctt tattgtgttc attcacaaat   1440
aatggcttag ctgaatagtt tgtaatttga ttttctttt tattactcca agccaacaga   1500
tatttagaat gaaacacccc aataatgtta tcaatatctc cctcgtacac tggatatcta   1560
gtgtatggct tattcataac cgtttcataa acttcttcgt atgtcgcatt tgaagcaaat   1620
gccgtcacat taattctagg tgttgtatct acatctttta cttttaaatt ttcaaaatta   1680
atgacacctt ccaacctact cgtctcaatt tcatttaaag caccttcatg tccagcaatt   1740
gctaacattg ttttaaattc ttcttttgaa aattgatgtt cttgaggttg cccttagat    1800 aaacttcgat taatactgtc cgtcaactta tttaaaagta atgtgatagg acggaacaca   1860
atgacacaaa tattaataat tggatataca agccttgtta tttatctgg aaatgttgca   1920 gcgacagact tgggaatcac ttcggagatc aaaatgataa caactgttaa aacagctgat   1980

```
gcaataccaa cgctaatccc ccaacgtaaa gccataattg taacaagtgt tggtaataaa    2040
atattcgcga cattattccc aattagaatc gttgtaataa actcacttgg tttttcaagt    2100
aactttacaa tgccttttgc ttttttatca cctttgtcag cttcagtttt aattttgct     2160 ttattggcag ccgttaatgc cgtctcgctt cctgaaaaga aaacgaaat aaatatcaat     2220 ataattatgg caatgatc                                                  2238
```

<210> SEQ ID NO 12
<211> LENGTH: 7975
<212> TYPE: DNA
<213> ORGANISM: Staphylococcus aureus

<400> SEQUENCE: 12

```
gatcaaacga caattattaa ttcgttaacg tttactgaaa cagtaccaaa tagaagttat      60
gcaagagcaa gtgcgaatga atcactagt aaaacagtta gtaatgtcag tcgtactgga     120
aataatgcca atgtcacagt aactgttact tatcaagatg aacaacatc aacagtgact     180 gtacctgtaa agcatgtcat tccagaaatc gttgcacatt cgcattacac tgtacaaggc    240
caagacttcc cagcaggtaa tggttctagt gcatcagatt actttaagtt atctaatggt    300
agtgacattg cagatgcaac tattacatgg gtaagtggac aagcgccaaa taagataat     360 acacgtattg tgaagatat aactgtaact gcacatatct taattgatgg cgaaacaacg     420
ccgattacga aaacagcaac atataaagta gtaagaactg taccgaaaca tgtctttgaa    480
acagccagag gtgttttata cccaggtgtt tcagatatgt atgatgcgaa acaatatgtt    540
aagccagtaa ataattcttg gtcgacaaat gcgcaacata tgaatttcca atttgttgga   600
acatatggtc ctaacaaaga tgttgtaggc atatctactc gtcttattag agtgacatat    660
gataatagac aaacagaaga tttaactatt ttatctaaag ttaaacctga cccacctaga    720
attgacgcaa actctgtgac atataaagca ggtcttacaa accaagaaat taagttaat    780 aacgtattaa ataactcgtc agtaaaatta tttaaagcag ataatacacc attaaatgtc    840
acaaatatta ctcatggtag cggttttagt tcggttgtga cagtaagtga cgcgttacca    900
aatggcggaa ttaaagcaaa atcttcaatt tcaatgaaca atgtgacgta tacgacgcaa    960
gacgaacatg gtcaagttgt tacagtaaca agaaatgaat ctgttgattc aaatgacagt   1020
gcaacagtaa cagtgacacc acaattacaa gcaactactg aaggcgctgt atttattaaa   1080
ggtggcgacg gttttgattt cggacacgta gaaagattta ttcaaaaccc gccacatggg   1140
gcaacggttg catggcatga tagtccagat acatggaaga atacagtcgg taacactcat   1200
aaaactgcgg ttgtaacatt acctaatggt caagtacgc gtaatgttga agttccagtc    1260
aaagtttatc cagttgctaa tgcaaaggcg ccatcacgtg atgtgaaagg tcaaaatttg   1320
actaatggaa cggatgcgat gaactacatt acatttgatc caaatacaaa acaaatggt    1380 atcactgcag catgggcaaa tagacaacaa ccaaataacc aacaagcagg cgtgcaacat   1440
ttaaatgtcg atgtcacata tccaggtatt tcagctgcta acgagttcc tgttactgtt    1500 aatgtatatc aatttgaatt ccctcaaact acttatacga caacggttgg aggcacttta   1560
gcaagtggta cgcaagcatc aggatatgca catatgcaaa atgctactgg tttaccaaca   1620
gatggattta cgtataaatg gaatcgtgat actacaggta caaatgacgc aaactggtca   1680
gctatgaata aaccgaatgt ggctaaagtc gttaacgcaa aatatgacgt catctataac   1740
ggacatactt ttgcaacatc tttaccagcg aaatttgtag taaagatgt gcaaccagcg    1800 aaaccaactg tgactgaaac agcggcagga gcgattacaa ttgcacctgg agcaaaccaa   1860
```

```
acagtgaata cacatgccgg taacgtaacg acatacgctg ataaattagt tattaaacgt   1920
aatggtaacg ttgtgacgac atttacacgt cgcaataata cgagtccatg ggtgaaagaa   1980
gcatctgcag caactgtagc aggtattgct ggaactaata atggtattac tgttgcagca   2040
ggtactttca accctgctga tacaattcaa gttgttgcaa cgcaaggaag cggagagaca   2100
gtgagtgatg agcaacgtag tgatgatttc acagttgtcg caccacaacc gaaccaagcg   2160
actactaaga tttggcaaaa tggtcatatt gatatcacgc ctaataatcc atcaggacat   2220
ttaattaatc caactcaagc aatggatatt gcttacactg aaaaagtggg taatggtgca   2280
gaacatagta agacaattaa tgttgttcgt ggtcaaaata atcaatggac aattgcgaat   2340
aagcctgact atgtaacgtt agatgcacaa actggtaaag tgacgttcaa tgccaatact   2400
ataaaaccaa attcatcaat cacaattact ccgaaagcag gtacaggtca ctcagtaagt   2460
agtaatccaa gtacattaac tgcaccggca gctcatactg tcaacacaac tgaaattgtg   2520
aaagattatg gttcaaatgt aacagcagct gaaattaaca atgcagttca agttgctaat   2580
aaacgtactg caacgattaa aaatggcaca gcaatgccta ctaatttagc tggtggtagc   2640
acaacgacga ttcctgtgac agtaacttac aatgatggta gtactgaaga agtacaagag   2700
tccattttca caaaagcgga taaacgtgag ttaatcacag ctaaaaatca tttagatgat   2760
ccagtaagca ctgaaggtaa aaagccaggt acaattacgc agtacaataa tgcaatgcat   2820
aatgcgcaac aacaaatcaa tactgcgaaa acagaagcac aacaagtgat taataatgag   2880
cgtgcaacac cacaacaagt ttctgacgca ctaactaaag ttcgtgcagc acaaactaag   2940
attgatcaag ctaaagcatt acttcaaaat aaagaagata atagccaatt agtaacgtct   3000
aaaaataact tacaaagttc tgtgaaccaa gtaccatcaa ctgctggtat gacgcaacaa   3060
agtattgata actataatgc gaagaagcgt gaagcagaaa ctgaaataac tgcagctcaa   3120
cgtgttattg acaatggcga tgcaactgca caacaaattt cagatgaaaa acatcgtgtc   3180
gataacgcat taacagcatt aaaccaagcg aaacatgatt taactgcaga tacacatgcc   3240
ttagagcaag cagtgcaaca attgaatcgc acaggtacaa cgactggtaa gaagccggca   3300
agtattactg cttacaataa ttcgattcgt gcacttcaaa gtgacttaac aagtgctaaa   3360
aatagcgcta atgctattat tcaaaagcca ataagaacag tacaagaagt gcaatctgcg   3420
ttaacaaatg taaatcgtgt caatgagcga ttaacgcaag caattaatca attagtacct   3480
ttagctgata atagtgcttt aaaaactgct aagacgaaac ttgatgaaga atcaataaaa   3540
tcagtaacta ctgatggtat gacacaatca tcaatccaag catatgaaaa tgctaaacgt   3600
gcgggtcaaa cagaatcaac aaatgcacaa aatgttatta acaatggtga tgcgactgac   3660
caacaaattg ccgcagaaaa aacaaaagta gaagaaaaat ataatagctt aaaacaagca   3720
attgctggat taactccaga cttggcacca ttacaaactg caaaaactca gttgcaaaat   3780
gatattgatc agccaacgag tacgactggt atgacaagcg catctattgc agcatttaat   3840
gaaaaacttt cagcagctag aactaaaatt caagaaattg atcgtgtatt agcctcacat   3900
ccagatgttg cgacaatacg tcaaaacgtg acagcagcga atgccgctaa atcagcactt   3960
gatcaagcac gtaatggctt aacagtcgat aaagcgcctt tagaaaatgc gaaaaatcaa   4020
ctacaatata gtattgacac gcaaacaagt acaactggta tgcacaagag ctctataaat   4080
gcatacaatg cgaagttaac agctgcacgt aataagattc aacaaatcaa tcaagtatta   4140
gcaggttcac cgactgtaga acaaattaat acaaatacgt ctacagcaaa tcaagctaaa   4200
tctgatttag atcatgcacg tcaagcttta acaccagata aagcgccgct tcaaactgcg   4260
```

```
aaaacgcaat tagaacaaag cattaatcaa ccaacggata caacaggtat gacgaccgct    4320
tcgttaaatg cgtacaacca aaaattacaa gcagcgcgtc aaaagttaac tgaaattaat    4380
caagtgttga atggcaaccc aactgtccaa aatatcaatg ataaagtgac agaggcaaac    4440
caagctaagg atcaattaaa tacagcacgt caaggtttaa cattagatag acagccagcg    4500
ttaacaacat tacatggtgc atctaactta aaccaagcac aacaaaataa tttcacgcaa    4560
caaattaatg ctgctcaaaa tcatgctgcg cttgaaacaa ttaagtctaa cattacggct    4620
ttaaatactg cgatgacgaa attaaaagac agtgttgcgg ataataatac aattaaatca    4680
gatcaaaatt acactgacgc aacaccagct aataaacaag cgtatgataa tgcagttaat    4740
gcggctaaag gtgtcattgg agaaacgact aatccaacga tggatgttaa cacagtgaac    4800
caaaaagcag catctgttaa atcgacgaaa gatgctttag atggtcaaca aaacttacaa    4860
cgtgcgaaaa cagaagcaac aaatgcgatt acgcatgcaa gtgatttaaa ccaagcacaa    4920
aagaatgcat taacacaaca agtgaatagt gcacaaaacg tgcaagcagt aaatgatatt    4980
aaacaaacga ctcaaagctt aaatactgct atgacaggtt aaaacgtgg cgttgctaat    5040 cataaccaag tcgtacaaag tgataattat gtcaacgcag atactaataa gaaaaatgat    5100
tacaacaatg catcaaacca tgcgaatgac attattaatg gtaatgcaca acatccagtt    5160
ataacaccaa gtgatgttaa caatgcttta tcaaatgtca caagtaaaga acatgcattg    5220
aatggtgaag ctaagttaaa tgctgcgaaa caagaagcga atactgcatt aggtcattta    5280
aacaatttaa ataatgcaca acgtcaaaac ttacaatcgc aaattaatgg tgcgcatcaa    5340
attgatgcag ttaatacaat taagcaaaat gcaacaaact tgaatagtgc aatgggtaac    5400
ttaagacaag ctgttgcaga taaagatcaa gtgaaacgta cagaagatta tgcggatgca    5460
gatacagcta acaaaaatgc atataacagt gcagtttcaa gtgccgaaac aatcattaat    5520
caaacaacaa atccaacgat gtctgttgat gatgttaatc gtgcaacttc agctgttact    5580
tctaataaaa atgcattaaa tggttatgaa aaattagcac aatctaaaac agatgctgca    5640
agagcaattg atgcattacc acatttaaat aatgcacaaa aagcagatgt taaatctaaa    5700
attaatgctg catcaaatat tgctggcgta aatactgtta acaacaagg tacagattta    5760 aatacagcga tgggtaactt gcaaggtgca atcaatgatg aacaaacgac gcttaatagt    5820
caaaactatc aagatgcgac acctagtaag aaaacagcat acacaaatgc ggtacaagct    5880
gcgaaagata ttttaaataa atcaaatggt caaaataaaa cgaaagatca agttactgaa    5940
gcgatgaatc aagtgaattc tgctaaaaat aacttagatg gtacgcgttt attagatcaa    6000
gcgaagcaaa cagcaaaaca gcagttaaat aatatgacgc atttaacaac tgcacaaaaa    6060
acgaatttaa caaaccaaat taatagtggt actactgtcg ctggtgttca aacggttcaa    6120
tcaaatgcca atacattaga tcaagccatg aatacgttaa dacaaagtat tgccaacaaa    6180
gatgcgacta agcaagtga agattacgta gatgctaata atgataagca aacagcatat    6240
aacaacgcag tagctgctgc tgaaacgatt attaatgcta atagtaatcc agaaatgaat    6300
ccaagtacga ttacacaaaa agcagagcaa gtgaatagtt ctaaaacggc acttaacggt    6360
gatgaaaact tagctgctgc aaaacaaaat gcgaaaacgt acttaaacac attgacaagt    6420
attacagatg ctcaaaagaa caatttgatt agtcaaatta ctagtgcgac aagagtgagt    6480
ggtgttgata ctgtaaaaca aaatgcgcaa catctagacc aagctatggc tagcttacag    6540
aatggtatta acaacgaatc tcaagtgaaa tcatctgaga aatatcgtga tgctgataca    6600
aataaacaac aagagtatga taatgctatt actgcagcga aagcgatttt aaataaatcg    6660
```

```
acaggtccaa acactgcgca aaatgcagtt gaagcagcat tacaacgtgt taataatgcg    6720
aaagatgcat tgaatggtga tgcaaaatta attgcagctc aaaacgcagc gaaacaacat    6780
ttaggtactt taacgcatat cactacagct caacgtaatg atttaacaaa tcaaatttca    6840
caagctacaa acttagctgg tgttgaatct gttaaacaaa atgcgaatag tttagatggt    6900
gctatgggta acttcaaaac ggctatcaac gataagtcag gaacattagc gagccaaaac    6960
ttcttggatg ctgatgagca aaaacgtaat gcatacaatc aagctgtatc agcagccgaa    7020
accattttaa ataaacaaac tggaccgaat acagcgaaaa cagcagtcga caagcactt    7080 aataatgtta ataatgcgaa acatgcatta aatggtacgc aaaacttaaa caatgcgaaa    7140
caagcagcga ttacagcaat caatggcgca tctgatttaa atcaaaaaca aaagatgca    7200 ttaaaagcac aagctaatgg tgctcaacgc gtatctaatg cacaagatgt acagcacaat    7260
gcgactgaac tgaacacggc aatgggcaca ttaaaacatg ccatcgcaga taagacgaat    7320
acgttagcaa gcagtaaata tgttaatgcc gatagcacta acaaaatgc ttacacaact    7380 aaagttacca atgctgaaca tattattagc ggtacgccaa cggttgttac gacaccttca    7440
gaagtaacag ctgcagctaa tcaagtaaac agcgcgaaac aagaattaaa tggtgacgaa    7500
agattacgtg aagcaaaaca aaacgccaat actgctattg atgcattaac acaattaaat    7560
acacctcaaa aagctaaatt aaaagaacaa gtgggacaag ccaatagatt agaagacgta    7620
caaactgttc aaacaaatgg acaagcattg aacaatgcaa tgaaaggctt aagagatagt    7680
attgctaacg aaacaacagt caaaacaagt caaaactata cagacgcaag tccgaataac    7740
caatcaacat ataatagcgc tgtgtcaaat gcgaaaggta tcattaatca aactaacaat    7800
ccgactatgg atactagtgc gattacccaa gctacaacac aagtgaataa tgctaaaaat    7860
ggtttaaacg gtgctgaaaa cttaagaaat gcacaaaaca ctgctaagca aaacttaaat    7920
acattatcac acttaacaaa taaccaaaaa tctgccatct catcacaaat tgatc    7975

<210> SEQ ID NO 13
<211> LENGTH: 2001
<212> TYPE: DNA
<213> ORGANISM: Staphylococcus aureus

<400> SEQUENCE: 13
gatcatggca ttgtatttaa tgcaagtcta cctttgtaca aagatgccat ccatcaaaaa      60
ggatcaatgc gcagtaatga caatggtgat gatatgagta tgatggtggg tacagtgctg     120
agtggctttg aatatcgagc gcaaaaagaa aagtatgata acttatataa attcttcaaa     180
gaaaatgaaa agaaatatca atatacaggc tttacaaaag aggcaattaa caagacacaa     240
aatgtcggat ataaaaatga atattttat attacatact cttctagaag tttaaaagaa     300
tatcgaaagt attatgaacc actgattcga aaaaatgata agaatttaa agaaggaatg     360 gaacgagcaa gaaaagaagt gaattacgct gcaaatacag atgctgttgc tacactttt     420 tctactaaga aaaactttac taaagacaat acagtagatg atgtaatcga actaagtgat     480
aaattatata atttaaaaaa taaccagat aaatctcaaa tcacaataca aatagggaaa     540
cccactatta atactaagaa agccttttat gatgataatc gtccaataga atatggggtg     600
cacagtaaag atgaataaaa ttaatgatag ggatttaaca gaattaagta gttactggg     660 ttatcaaaat attgatataa aaaagaatt taaagttaat ggaaaaaggt ttaaacaagt     720
agacagttat aatgatgata agaatagtaa tttgaatggt gctgctgata ttaaaatata     780
tgagttatta gatgataaaa gtaaaccaac tggtcaacag acaataattt atcaaggaac     840
```

```
atctaatgag gcaattaatc caaataatcc attaaaatca tcggggtttg gagatgattg    900
gctccaaaat gctaaattaa tgaataatga taatgaaagc acagattatt taaagcaaac    960
agatcaatta tcaaatcaat ataaaataaa gttagaagat gcagatagat tatcaaatag   1020 tgattttta  aaaaaatata gaatggaatc aagtaacttc aaaaacaaaa ccattgtggc   1080
ggatggcggt aattcggaag gcggtgcagg agcaaaatat caaggagcga acatccgaa    1140 tgaaaaagtt gttgctactg actcagcaat gattccttat gctgcttggc agaaatttgc   1200
tagaccacgc tttgataata tgattagttt taatagtacc aacgattat  taacatggtt   1260 acaagatcca ttcatcaaag atatgccagg aaaacgcgtt aacattaatg atggtgtgcc   1320
caggttagat actttaatag acagccatgt aggttataaa aggaagttaa atagaaaaga   1380
taacacatac gatactgtac cactaatcaa aataaagtcg gtaaaagata cagaaattaa   1440
aaatggaaaa aaagtaaaaa agactattaa cataacatta gatatggatg gcgaattcc    1500 aataaatgtt tggacaggag attcgattgc acgttctgga agaggaactt taattaaact   1560
taatttagaa aatcttgatg cgttgagtaa actgattact ggtgaaacaa gtggtatgtt   1620
agcagaatgc gtaatctttt taaatgaaag ttttaacatc tcagaaaatg aaaataaaaa   1680
ttttgcagat agaaagaaac aattatcaga aggatttaag gataagatta acttatttca   1740
gttagaagaa atggaaagaa ctttaattag taaaataaac tcacttgaag aagttgcaga   1800
tgaaacaata gaaagtatta gtgctgttaa acacttatta cctgattttg cattggatgc   1860
attaaaagaa agaattaatg agttgtttaa aggtataaaa tcttttatag aaaaagtgta   1920
tgatagtata gataatgaaa ttttagaaat tttcaaaaat atagatcacg acttcagaga   1980
tggagtatct gaagaaatga t                                             2001
```

<210> SEQ ID NO 14
<211> LENGTH: 106
<212> TYPE: PRT
<213> ORGANISM: Staphylococcus aureus

<400> SEQUENCE: 14

Asp Gln Thr Lys Thr Gln Thr Ala His Thr Val Lys Thr Ala Gln Thr
1               5                   10                  15

Ala Gln Glu Gln Asn Lys Val Gln Thr Pro Val Lys Asp Val Ala Thr
            20                  25                  30

Ala Lys Ser Glu Ser Asn Asn Gln Ala Val Ser Asp Asn Lys Ser Gln
        35                  40                  45

Gln Thr Asn Lys Val Thr Lys His Asn Glu Thr Pro Lys Gln Ala Ser
    50                  55                  60

Lys Ala Lys Glu Leu Pro Lys Thr Gly Leu Thr Ser Val Asp Asn Phe
65                  70                  75                  80

Ile Ser Thr Val Ala Phe Ala Thr Leu Ala Leu Leu Gly Ser Leu Ser
                85                  90                  95

Leu Leu Leu Phe Lys Arg Lys Glu Ser Lys
            100                 105

<210> SEQ ID NO 15
<211> LENGTH: 960
<212> TYPE: PRT
<213> ORGANISM: Staphylococcus aureus

<400> SEQUENCE: 15

Asp Arg Ile Ile Glu Thr Ala Pro Thr Asp Tyr Leu Ser Trp Gly Val
1               5                   10                  15

-continued

Gly Ala Val Gly Asn Pro Arg Phe Ile Asn Val Glu Ile Val His Thr
        20                  25                  30

His Asp Tyr Ala Ser Phe Ala Arg Ser Met Asn Asn Tyr Ala Asp Tyr
        35                  40                  45

Ala Ala Thr Gln Leu Gln Tyr Tyr Gly Leu Lys Pro Asp Ser Ala Glu
    50                  55                  60

Tyr Asp Gly Asn Gly Thr Val Trp Thr His Tyr Ala Val Ser Lys Tyr
65                  70                  75                  80

Leu Gly Gly Thr Asp His Ala Asp Pro His Gly Tyr Leu Arg Ser His
            85                  90                  95

Asn Tyr Ser Tyr Asp Gln Leu Tyr Asp Leu Ile Asn Glu Lys Tyr Leu
            100                 105                 110

Ile Lys Met Gly Lys Val Ala Pro Trp Gly Thr Gln Ser Thr Thr Thr
            115                 120                 125

Pro Thr Thr Pro Ser Lys Pro Thr Thr Pro Ser Lys Pro Ser Thr Gly
    130                 135                 140

Lys Leu Thr Val Ala Ala Asn Asn Gly Val Ala Gln Ile Lys Pro Thr
145                 150                 155                 160

Asn Ser Gly Leu Tyr Thr Thr Val Tyr Asp Lys Thr Gly Lys Ala Thr
                165                 170                 175

Asn Glu Val Gln Lys Thr Phe Ala Val Ser Lys Thr Ala Thr Leu Gly
            180                 185                 190

Asn Gln Lys Phe Tyr Leu Val Gln Asp Tyr Asn Ser Gly Asn Lys Phe
        195                 200                 205

Gly Trp Val Lys Glu Gly Asp Val Val Tyr Asn Thr Ala Lys Ser Pro
    210                 215                 220

Val Asn Val Asn Gln Ser Tyr Ser Ile Lys Pro Gly Thr Lys Leu Tyr
225                 230                 235                 240

Thr Val Pro Trp Gly Thr Ser Lys Gln Val Ala Gly Ser Val Ser Gly
                245                 250                 255

Ser Gly Asn Gln Thr Phe Lys Ala Ser Lys Gln Gln Gln Ile Asp Lys
            260                 265                 270

Ser Ile Tyr Leu Tyr Gly Ser Val Asn Gly Lys Ser Gly Trp Val Ser
        275                 280                 285

Lys Ala Tyr Leu Val Asp Thr Ala Lys Pro Thr Pro Thr Pro Thr Pro
    290                 295                 300

Lys Pro Ser Thr Pro Thr Thr Asn Asn Lys Leu Thr Val Ser Ser Leu
305                 310                 315                 320

Asn Gly Val Ala Gln Ile Asn Ala Lys Asn Asn Gly Leu Phe Thr Thr
                325                 330                 335

Val Tyr Asp Lys Thr Gly Lys Pro Thr Lys Glu Val Gln Lys Thr Phe
            340                 345                 350

Ala Val Thr Lys Glu Ala Ser Leu Gly Gly Asn Lys Phe Tyr Leu Val
        355                 360                 365

Lys Asp Tyr Asn Ser Pro Thr Leu Ile Gly Trp Val Lys Gln Gly Asp
    370                 375                 380

Val Ile Tyr Asn Asn Ala Lys Ser Pro Val Asn Val Met Gln Thr Tyr
385                 390                 395                 400

Thr Val Lys Pro Gly Thr Lys Leu Tyr Ser Val Pro Trp Gly Thr Tyr
                405                 410                 415

Lys Gln Glu Ala Gly Ala Val Ser Gly Thr Gly Asn Gln Thr Phe Lys
            420                 425                 430

Ala Thr Lys Gln Gln Gln Ile Asp Lys Ser Ile Tyr Leu Phe Gly Thr

```
                435                 440                 445
Val Asn Gly Lys Ser Gly Trp Val Ser Lys Ala Tyr Leu Ala Val Pro
450                 455                 460

Ala Ala Pro Lys Lys Ala Val Ala Gln Pro Lys Thr Ala Val Lys Ala
465                 470                 475                 480

Tyr Thr Val Thr Lys Pro Gln Thr Thr Gln Thr Val Ser Lys Ile Ala
                485                 490                 495

Gln Val Lys Pro Asn Asn Thr Gly Ile Arg Ala Ser Val Tyr Glu Lys
                500                 505                 510

Thr Ala Lys Asn Gly Ala Lys Tyr Ala Asp Arg Thr Phe Tyr Val Thr
                515                 520                 525

Lys Glu Arg Ala His Gly Asn Glu Thr Tyr Val Leu Leu Asn Asn Thr
                530                 535                 540

Ser His Asn Ile Pro Leu Gly Trp Phe Asn Val Lys Asp Leu Asn Val
545                 550                 555                 560

Gln Asn Leu Gly Lys Glu Val Lys Thr Thr Gln Lys Tyr Thr Val Asn
                565                 570                 575

Lys Ser Asn Asn Gly Leu Ser Met Val Pro Trp Gly Thr Lys Asn Gln
                580                 585                 590

Val Ile Leu Thr Gly Asn Asn Ile Ala Gln Gly Thr Phe Asn Ala Thr
                595                 600                 605

Lys Gln Val Ser Val Gly Lys Asp Val Tyr Leu Tyr Gly Thr Ile Asn
                610                 615                 620

Asn Arg Thr Gly Trp Val Asn Ala Lys Asp Leu Thr Ala Pro Thr Ala
625                 630                 635                 640

Val Lys Pro Thr Thr Ser Ala Ala Lys Asp Tyr Asn Tyr Thr Tyr Val
                645                 650                 655

Ile Lys Asn Gly Asn Gly Tyr Tyr Tyr Val Thr Pro Asn Ser Asp Thr
                660                 665                 670

Ala Lys Tyr Ser Leu Lys Ala Phe Asn Glu Gln Pro Phe Ala Val Val
                675                 680                 685

Lys Glu Gln Val Ile Asn Gly Gln Thr Trp Tyr Tyr Gly Lys Leu Ser
                690                 695                 700

Asn Gly Lys Leu Ala Trp Ile Lys Ser Thr Asp Leu Ala Lys Glu Leu
705                 710                 715                 720

Ile Lys Tyr Asn Gln Thr Gly Met Ala Leu Asn Gln Val Ala Gln Ile
                725                 730                 735

Gln Ala Gly Leu Gln Tyr Lys Pro Gln Val Gln Arg Val Pro Gly Lys
                740                 745                 750

Trp Thr Gly Ala Asn Phe Asn Asp Val Lys His Ala Met Asp Thr Lys
                755                 760                 765

Arg Leu Ala Gln Asp Pro Ala Leu Lys Tyr Gln Phe Leu Arg Leu Asp
770                 775                 780

Gln Pro Gln Asn Ile Ser Ile Asp Lys Ile Asn Gln Phe Leu Lys Gly
785                 790                 795                 800

Lys Gly Val Leu Glu Asn Gln Gly Ala Ala Phe Asn Lys Ala Ala Gln
                805                 810                 815

Met Tyr Gly Ile Asn Glu Val Tyr Leu Ile Ser His Ala Leu Leu Glu
                820                 825                 830

Thr Gly Asn Gly Thr Ser Gln Leu Ala Lys Gly Ala Asp Val Val Asn
                835                 840                 845

Asn Lys Val Val Thr Asn Ser Asn Thr Lys Tyr His Asn Val Phe Gly
850                 855                 860
```

```
Ile Ala Ala Tyr Asp Asn Asp Pro Leu Arg Glu Gly Ile Lys Tyr Ala
865                 870                 875                 880

Lys Gln Ala Gly Trp Asp Thr Val Ser Lys Ala Ile Val Gly Gly Ala
            885                 890                 895

Lys Phe Ile Gly Asn Ser Tyr Val Lys Ala Gly Gln Asn Thr Leu Tyr
            900                 905                 910

Lys Met Arg Trp Asn Pro Ala His Pro Gly Thr His Gln Tyr Ala Thr
            915                 920                 925

Asp Val Asp Trp Ala Asn Ile Asn Ala Lys Ile Ile Lys Gly Tyr Tyr
            930                 935                 940

Asp Lys Ile Gly Glu Val Gly Lys Tyr Phe Asp Ile Pro Gln Tyr Lys
945                 950                 955                 960

<210> SEQ ID NO 16
<211> LENGTH: 386
<212> TYPE: PRT
<213> ORGANISM: Staphylococcus aureus

<400> SEQUENCE: 16

Asp Gln Tyr Ser Glu Asp Ala Lys Lys Thr Gln Lys Asp Tyr Ala Ser
1               5                   10                  15

Gln Ser Lys Lys Asp Lys Asn Glu Lys Ser Asn Thr Lys Asn Pro Gln
            20                  25                  30

Leu Pro Thr Gln Asp Glu Leu Lys His Lys Ser Lys Pro Ala Gln Ser
            35                  40                  45

Phe Asn Asn Asp Val Asn Gln Lys Asp Thr Arg Ala Thr Ser Leu Phe
50                  55                  60

Glu Thr Asp Pro Ser Ile Ser Asn Asn Asp Ser Gly Gln Phe Asn
65                  70                  75                  80

Val Val Asp Ser Lys Asp Thr Arg Gln Phe Val Lys Ser Ile Ala Lys
            85                  90                  95

Asp Ala His Arg Ile Gly Gln Asp Asn Asp Ile Tyr Ala Ser Val Met
            100                 105                 110

Ile Ala Gln Ala Ile Leu Glu Ser Asp Ser Gly Arg Ser Ala Leu Ala
            115                 120                 125

Lys Ser Pro Asn His Asn Leu Phe Gly Ile Lys Gly Ala Phe Glu Gly
            130                 135                 140

Asn Ser Val Pro Phe Asn Thr Leu Glu Ala Asp Gly Asn Gln Leu Tyr
145                 150                 155                 160

Ser Ile Asn Ala Gly Phe Arg Lys Tyr Pro Ser Thr Lys Glu Ser Leu
            165                 170                 175

Lys Asp Tyr Ser Asp Leu Ile Lys Asn Gly Ile Asp Gly Asn Arg Thr
            180                 185                 190

Ile Tyr Lys Pro Thr Trp Lys Ser Glu Ala Asp Ser Tyr Lys Asp Ala
            195                 200                 205

Thr Ser His Leu Ser Lys Thr Tyr Ala Thr Asp Pro Asn Tyr Ala Lys
            210                 215                 220

Lys Leu Asn Ser Ile Ile Lys His Tyr Gln Leu Thr Gln Phe Asp Asp
225                 230                 235                 240

Glu Arg Met Pro Asp Leu Asp Lys Tyr Glu Arg Ser Ile Lys Asp Tyr
            245                 250                 255

Asp Asp Ser Ser Asp Glu Phe Lys Pro Phe Arg Glu Val Ser Asp Ser
            260                 265                 270

Met Pro Tyr Pro His Gly Gln Cys Thr Trp Tyr Val Tyr Asn Arg Met
            275                 280                 285
```

```
Lys Gln Phe Gly Thr Ser Ile Ser Gly Asp Leu Gly Asp Ala His Asn
            290                 295                 300

Trp Asn Asn Arg Ala Gln Tyr Arg Asp Tyr Gln Val Ser His Thr Pro
305                 310                 315                 320

Lys Arg His Ala Ala Val Val Phe Glu Ala Gly Gln Phe Gly Ala Asp
                325                 330                 335

Gln His Tyr Gly His Val Ala Phe Val Glu Lys Val Asn Ser Asp Gly
                340                 345                 350

Ser Ile Val Ile Ser Glu Ser Asn Val Lys Gly Leu Gly Ile Ile Ser
            355                 360                 365

His Arg Thr Ile Asn Ala Ala Ala Ala Glu Glu Leu Ser Tyr Ile Thr
370                 375                 380

Gly Lys
385

<210> SEQ ID NO 17
<211> LENGTH: 325
<212> TYPE: PRT
<213> ORGANISM: Staphylococcus aureus

<400> SEQUENCE: 17

Met Lys Met Asn Lys Leu Val Lys Ser Ser Val Ala Thr Ser Met Ala
1               5                   10                  15

Leu Leu Leu Leu Ser Gly Thr Ala Asn Ala Glu Gly Lys Ile Thr Pro
            20                  25                  30

Val Ser Val Lys Lys Val Asp Asp Lys Val Thr Leu Tyr Lys Thr Thr
        35                  40                  45

Ala Thr Ala Asp Ser Asp Lys Phe Lys Ile Ser Gln Ile Leu Thr Phe
    50                  55                  60

Asn Phe Ile Lys Asp Lys Ser Tyr Asp Lys Asp Thr Leu Val Leu Lys
65                  70                  75                  80

Ala Thr Gly Asn Ile Asn Ser Gly Phe Val Lys Pro Asn Pro Asn Asp
                85                  90                  95

Tyr Asp Phe Ser Lys Leu Tyr Trp Gly Ala Lys Tyr Asn Val Ser Ile
            100                 105                 110

Ser Ser Gln Ser Asn Asp Ser Val Asn Val Val Asp Tyr Ala Pro Lys
        115                 120                 125

Asn Gln Asn Glu Glu Phe Gln Val Gln Asn Thr Leu Gly Tyr Thr Phe
    130                 135                 140

Gly Gly Asp Ile Ser Ile Ser Asn Gly Leu Ser Gly Gly Leu Asn Gly
145                 150                 155                 160

Asn Thr Ala Phe Ser Glu Thr Ile Asn Tyr Lys Gln Glu Ser Tyr Arg
                165                 170                 175

Thr Thr Leu Ser Arg Asn Thr Asn Tyr Lys Asn Val Gly Trp Gly Val
            180                 185                 190

Glu Ala His Lys Ile Met Asn Asn Gly Trp Gly Pro Tyr Gly Arg Asp
        195                 200                 205

Ser Phe His Pro Thr Tyr Gly Asn Glu Leu Phe Leu Ala Gly Arg Gln
    210                 215                 220

Ser Ser Ala Tyr Ala Gly Gln Asn Phe Ile Ala Gln His Gln Met Pro
225                 230                 235                 240

Leu Leu Ser Arg Ser Asn Phe Asn Pro Glu Phe Leu Ser Val Leu Ser
                245                 250                 255

His Arg Gln Asp Gly Ala Lys Lys Ser Lys Ile Thr Val Thr Tyr Gln
            260                 265                 270
```

```
Arg Glu Met Asp Leu Tyr Gln Ile Arg Trp Asn Gly Phe Tyr Trp Ala
    275                 280                 285

Gly Ala Asn Tyr Lys Asn Phe Lys Thr Arg Thr Phe Lys Ser Thr Tyr
290                 295                 300

Glu Ile Asp Trp Glu Asn His Lys Val Lys Leu Leu Asp Thr Lys Glu
305                 310                 315                 320

Thr Glu Asn Asn Lys
            325

<210> SEQ ID NO 18
<211> LENGTH: 157
<212> TYPE: PRT
<213> ORGANISM: Staphylococcus aureus

<400> SEQUENCE: 18

Ser Phe Asn Tyr Ser Lys Ser Ile Ser Tyr Thr Gln Gln Asn Tyr Val
1               5                   10                  15

Ser Glu Val Glu Gln Gln Asn Ser Lys Ser Val Leu Trp Gly Val Lys
                20                  25                  30

Ala Asn Ser Phe Ala Thr Glu Ser Gly Gln Lys Ser Ala Phe Asp Ser
            35                  40                  45

Asp Leu Phe Val Gly Tyr Lys Pro His Ser Lys Asp Pro Arg Asp Tyr
    50                  55                  60

Phe Val Pro Asp Ser Glu Leu Pro Pro Leu Val Gln Ser Gly Phe Asn
65                  70                  75                  80

Pro Ser Phe Ile Ala Thr Val Ser His Glu Lys Gly Ser Ser Asp Thr
                85                  90                  95

Ser Glu Phe Glu Ile Thr Tyr Gly Arg Asn Met Asp Val Thr His Ala
            100                 105                 110

Ile Lys Arg Ser Thr His Tyr Gly Asn Ser Tyr Leu Asp Gly His Arg
    115                 120                 125

Val His Asn Ala Phe Val Asn Arg Asn Tyr Thr Val Lys Tyr Glu Val
130                 135                 140

Asn Trp Lys Thr His Glu Ile Lys Val Lys Gly Gln Asn
145                 150                 155

<210> SEQ ID NO 19
<211> LENGTH: 345
<212> TYPE: PRT
<213> ORGANISM: Staphylococcus aureus

<400> SEQUENCE: 19

Ile Ile Ala Ile Ile Ile Leu Ile Phe Ile Ser Phe Phe Ser Gly
1               5                   10                  15

Ser Glu Thr Ala Leu Thr Ala Ala Asn Lys Ala Lys Phe Lys Thr Glu
                20                  25                  30

Ala Asp Lys Gly Asp Lys Lys Ala Lys Gly Ile Val Lys Leu Leu Glu
            35                  40                  45

Lys Pro Ser Glu Phe Ile Thr Thr Ile Leu Ile Gly Asn Asn Val Ala
    50                  55                  60

Asn Ile Leu Leu Pro Thr Leu Val Thr Ile Met Ala Leu Arg Trp Gly
65                  70                  75                  80

Ile Ser Val Gly Ile Ala Ser Ala Val Leu Thr Val Val Ile Ile Leu
                85                  90                  95

Ile Ser Glu Val Ile Pro Lys Ser Val Ala Ala Thr Phe Pro Asp Lys
            100                 105                 110

Ile Thr Arg Leu Val Tyr Pro Ile Ile Asn Ile Cys Val Ile Val Phe
```

```
                    115                 120                 125
Arg Pro Ile Thr Leu Leu Asn Lys Leu Thr Asp Ser Ile Asn Arg
    130                 135                 140
Ser Leu Ser Lys Gly Gln Pro Gln Glu His Gln Phe Ser Lys Glu Glu
145                 150                 155                 160
Phe Lys Thr Met Leu Ala Ile Ala Gly His Glu Gly Ala Leu Asn Glu
                165                 170                 175
Ile Glu Thr Ser Arg Leu Glu Gly Val Ile Asn Phe Glu Asn Leu Lys
                180                 185                 190
Val Lys Asp Val Asp Thr Thr Pro Arg Ile Asn Val Thr Ala Phe Ala
            195                 200                 205
Ser Asn Ala Thr Tyr Glu Glu Val Tyr Glu Thr Val Met Asn Lys Pro
            210                 215                 220
Tyr Thr Arg Tyr Pro Val Tyr Glu Gly Asp Ile Asp Asn Ile Ile Gly
225                 230                 235                 240
Val Phe His Ser Lys Tyr Leu Leu Ala Trp Ser Asn Lys Lys Glu Asn
                245                 250                 255
Gln Ile Thr Asn Tyr Ser Ala Lys Pro Leu Phe Val Asn Glu His Asn
            260                 265                 270
Lys Ala Glu Trp Val Leu Arg Lys Met Thr Ile Ser Arg Lys His Leu
        275                 280                 285
Ala Ile Val Leu Asp Glu Phe Gly Gly Thr Glu Ala Ile Val Ser His
    290                 295                 300
Glu Asp Leu Ile Glu Glu Leu Leu Gly Met Glu Ile Glu Asp Glu Met
305                 310                 315                 320
Asp Lys Lys Glu Lys Glu Lys Leu Ser Gln Gln Gln Ile Gln Phe Gln
                325                 330                 335
Gln Arg Lys Asn Arg Asn Val Ser Ile
            340                 345

<210> SEQ ID NO 20
<211> LENGTH: 133
<212> TYPE: PRT
<213> ORGANISM: Staphylococcus aureus

<400> SEQUENCE: 20

Met Asn Lys Gln Gln Lys Glu Phe Lys Ser Phe Tyr Ser Ile Arg Lys
1               5                   10                  15
Ser Ser Leu Gly Val Ala Ser Val Ala Ile Ser Thr Leu Leu Leu Leu
            20                  25                  30
Met Ser Asn Gly Glu Ala Gln Ala Ala Ala Glu Glu Thr Gly Gly Thr
        35                  40                  45
Asn Thr Glu Ala Gln Pro Lys Thr Glu Ala Val Ala Ser Pro Thr Thr
    50                  55                  60
Thr Ser Glu Lys Ala Pro Glu Thr Lys Pro Val Ala Asn Ala Val Ser
65                  70                  75                  80
Val Ser Asn Lys Glu Val Glu Ala Pro Thr Ser Glu Thr Lys Glu Ala
                85                  90                  95
Lys Glu Val Lys Glu Val Lys Ala Pro Lys Glu Thr Lys Glu Val Lys
            100                 105                 110
Pro Ala Ala Lys Ala Thr Asn Asn Thr Tyr Pro Ile Leu Asn Gln Glu
        115                 120                 125
Leu Ile Arg Ser Asp
    130
```

-continued

```
<210> SEQ ID NO 21
<211> LENGTH: 205
<212> TYPE: PRT
<213> ORGANISM: Staphylococcus aureus

<400> SEQUENCE: 21

Asp His Gly Ile Val Phe Asn Ala Ser Leu Pro Leu Tyr Lys Asp Ala
1               5                   10                  15

Ile His Gln Lys Gly Ser Met Arg Ser Asn Asp Asn Gly Asp Asp Met
            20                  25                  30

Ser Met Met Val Gly Thr Val Leu Ser Gly Phe Glu Tyr Arg Ala Gln
        35                  40                  45

Lys Glu Lys Tyr Asp Asn Leu Tyr Lys Phe Phe Lys Glu Asn Glu Lys
    50                  55                  60

Lys Tyr Gln Tyr Thr Gly Phe Thr Lys Glu Ala Ile Asn Lys Thr Gln
65                  70                  75                  80

Asn Val Gly Tyr Lys Asn Glu Tyr Phe Tyr Ile Thr Tyr Ser Ser Arg
                85                  90                  95

Ser Leu Lys Glu Tyr Arg Lys Tyr Tyr Glu Pro Leu Ile Arg Lys Asn
            100                 105                 110

Asp Lys Glu Phe Lys Glu Gly Met Glu Arg Ala Arg Lys Glu Val Asn
        115                 120                 125

Tyr Ala Ala Asn Thr Asp Ala Val Ala Thr Leu Phe Ser Thr Lys Lys
    130                 135                 140

Asn Phe Thr Lys Asp Asn Thr Val Asp Val Ile Glu Leu Ser Asp
145                 150                 155                 160

Lys Leu Tyr Asn Leu Lys Asn Lys Pro Asp Lys Ser Thr Ile Thr Ile
                165                 170                 175

Gln Ile Gly Lys Pro Thr Ile Asn Thr Lys Lys Ala Phe Tyr Asp Asp
            180                 185                 190

Asn Arg Pro Ile Glu Tyr Gly Val His Ser Lys Asp Glu
        195                 200                 205

<210> SEQ ID NO 22
<211> LENGTH: 510
<212> TYPE: PRT
<213> ORGANISM: Staphylococcus aureus

<400> SEQUENCE: 22

Asp His Tyr Val Ile Gln Tyr Phe Ser Gly Leu Ile Gly Gly Arg Gly
1               5                   10                  15

Arg Arg Ala Asn Leu Tyr Gly Leu Phe Asn Lys Ala Ile Glu Phe Glu
            20                  25                  30

Asn Ser Ser Phe Arg Gly Leu Tyr Gln Phe Ile Arg Phe Ile Asp Glu
        35                  40                  45

Leu Ile Glu Arg Gly Lys Asp Phe Gly Glu Glu Asn Val Val Gly Pro
    50                  55                  60

Asn Asp Asn Val Val Arg Met Met Thr Ile His Ser Ser Lys Gly Leu
65                  70                  75                  80

Glu Phe Pro Phe Val Ile Tyr Ser Gly Leu Ser Lys Asp Phe Asn Lys
                85                  90                  95

Arg Asp Leu Lys Gln Pro Val Ile Leu Asn Gln Gln Phe Gly Leu Gly
            100                 105                 110

Met Asp Tyr Phe Asp Val Asp Lys Glu Met Ala Phe Pro Ser Leu Ala
        115                 120                 125

Ser Val Ala Tyr Arg Ala Val Ala Glu Lys Glu Leu Val Ser Glu Glu
    130                 135                 140
```

Met Arg Leu Val Tyr Val Ala Leu Thr Arg Ala Lys Glu Gln Leu Tyr
145                 150                 155                 160

Leu Ile Gly Arg Val Lys Asn Asp Lys Ser Leu Leu Glu Leu Glu Gln
                165                 170                 175

Leu Ser Ile Ser Gly Glu His Ile Ala Val Asn Glu Arg Leu Thr Ser
            180                 185                 190

Pro Asn Pro Phe His Leu Ile Tyr Ser Ile Leu Ser Lys His Gln Ser
        195                 200                 205

Ala Ser Ile Pro Asp Asp Leu Lys Phe Glu Lys Asp Ile Ala Gln Ile
    210                 215                 220

Glu Asp Ser Ser Arg Pro Asn Val Asn Ile Ser Ile Val Tyr Phe Glu
225                 230                 235                 240

Asp Val Ser Thr Glu Thr Ile Leu Asp Asn Asp Glu Tyr Arg Ser Val
                245                 250                 255

Asn Gln Leu Glu Thr Met Gln Asn Gly Asn Glu Asp Val Lys Ala Gln
                260                 265                 270

Ile Lys His Gln Leu Asp Tyr Arg Tyr Pro Tyr Val Asn Asp Thr Lys
            275                 280                 285

Lys Pro Ser Lys Gln Ser Val Ser Glu Leu Lys Arg Gln Tyr Glu Thr
        290                 295                 300

Glu Glu Ser Gly Thr Ser Tyr Glu Arg Val Arg Gln Tyr Arg Ile Gly
305                 310                 315                 320

Phe Ser Thr Tyr Glu Arg Pro Lys Phe Leu Ser Glu Gln Gly Lys Arg
                325                 330                 335

Lys Ala Asn Glu Ile Gly Thr Leu Met His Thr Val Met Gln His Leu
                340                 345                 350

Pro Phe Lys Lys Glu Arg Ile Ser Glu Val Leu His Gln Tyr Ile
            355                 360                 365

Asp Gly Leu Ile Asp Lys His Ile Ile Glu Ala Asp Ala Lys Lys Asp
    370                 375                 380

Ile Arg Met Asp Glu Ile Met Thr Phe Ile Asn Ser Glu Leu Tyr Ser
385                 390                 395                 400

Ile Ile Ala Glu Ala Glu Gln Val Tyr Arg Glu Leu Pro Phe Val Val
                405                 410                 415

Asn Gln Ala Leu Val Asp Gln Leu Pro Gln Gly Asp Gly Asp Val Ser
                420                 425                 430

Ile Ile Gln Gly Met Ile Asp Leu Ile Phe Val Lys Asp Gly Val His
            435                 440                 445

Tyr Phe Val Asp Tyr Lys Thr Asp Ala Phe Asn Arg Arg Gly Met
    450                 455                 460

Thr Asp Glu Glu Ile Gly Thr Gln Leu Lys Asn Lys Tyr Lys Ile Gln
465                 470                 475                 480

Met Lys Tyr Tyr Gln Asn Thr Leu Gln Thr Ile Leu Asn Lys Glu Val
                485                 490                 495

Lys Gly Tyr Leu Tyr Phe Phe Lys Phe Gly Thr Leu Gln Leu
            500                 505                 510

<210> SEQ ID NO 23
<211> LENGTH: 124
<212> TYPE: PRT
<213> ORGANISM: Staphylococcus aureus

<400> SEQUENCE: 23

Met Lys Phe Leu Ser Phe Lys Tyr Asn Asp Lys Thr Ser Tyr Gly Val
1               5                   10                  15

```
Lys Val Lys Arg Glu Asp Ala Val Trp Asp Leu Thr Gln Val Phe Ala
             20                  25                  30

Asp Phe Ala Glu Gly Asp Phe His Pro Lys Thr Leu Leu Ala Gly Leu
         35                  40                  45

Gln Gln Asn His Thr Leu Asp Phe Gln Glu Gln Val Arg Lys Ala Val
 50                  55                  60

Val Ala Ala Glu Asp Ser Gly Lys Ala Glu Asp Tyr Lys Ile Ser Phe
 65                  70                  75                  80

Asn Asp Ile Glu Phe Leu Pro Pro Val Thr Pro Pro Asn Asn Val Ile
                 85                  90                  95

Ala Phe Gly Arg Asn Tyr Lys Asp His Ala Asn Glu Leu Asn His Glu
            100                 105                 110

Val Glu Lys Leu Tyr Val Phe Thr Lys Ala Ala Ser
            115                 120

<210> SEQ ID NO 24
<211> LENGTH: 180
<212> TYPE: PRT
<213> ORGANISM: Staphylococcus aureus

<400> SEQUENCE: 24

Ser Gly Thr Gly Phe Ile Val Gly Lys Asn Thr Ile Val Thr Asn Lys
1               5                   10                  15

His Val Val Ala Gly Met Glu Ile Gly Ala His Ile Ala His Pro
             20                  25                  30

Asn Gly Glu Tyr Asn Asn Gly Gly Phe Tyr Lys Val Lys Lys Ile Val
         35                  40                  45

Arg Tyr Ser Gly Gln Glu Asp Ile Ala Ile Leu His Val Glu Asp Lys
 50                  55                  60

Ala Val His Pro Lys Asn Arg Asn Phe Lys Asp Tyr Thr Gly Ile Leu
 65                  70                  75                  80

Lys Ile Ala Ser Glu Ala Lys Glu Asn Glu Arg Ile Ser Ile Val Gly
                 85                  90                  95

Tyr Pro Glu Pro Tyr Ile Asn Lys Phe Gln Met Tyr Glu Ser Thr Gly
            100                 105                 110

Lys Val Leu Ser Val Lys Gly Asn Met Ile Ile Thr Asp Ala Phe Val
            115                 120                 125

Glu Pro Gly Asn Ser Gly Ser Ala Val Phe Asn Ser Lys Tyr Glu Val
        130                 135                 140

Val Gly Val His Phe Gly Gly Asn Gly Pro Gly Asn Lys Ser Thr Lys
145                 150                 155                 160

Gly Tyr Gly Val Tyr Phe Ser Pro Glu Ile Lys Lys Phe Ile Ala Asp
                165                 170                 175

Asn Thr Asp Lys
            180

<210> SEQ ID NO 25
<211> LENGTH: 239
<212> TYPE: PRT
<213> ORGANISM: Staphylococcus aureus

<400> SEQUENCE: 25

Met Asn Lys Asn Ile Ile Ile Lys Ser Ile Ala Ala Leu Thr Ile Leu
1               5                   10                  15

Thr Ser Ile Thr Gly Val Gly Thr Met Val Glu Gly Ile Gln Gln
             20                  25                  30
```

```
Thr Ala Lys Ala Glu Asn Thr Val Lys Gln Ile Thr Asn Thr Asn Val
            35                  40                  45

Ala Pro Tyr Ser Gly Val Thr Trp Met Gly Ala Thr Gly Phe Val
 50                  55                  60

Val Gly Asn His Thr Ile Ile Thr Asn Lys His Val Thr Tyr His Met
 65                  70                  75                  80

Lys Val Gly Asp Glu Ile Lys Ala His Pro Asn Gly Phe Tyr Asn Asn
                85                  90                  95

Gly Gly Gly Leu Tyr Lys Val Thr Lys Ile Val Asp Tyr Pro Gly Lys
            100                 105                 110

Glu Asp Ile Ala Val Val Gln Val Glu Lys Ser Thr Gln Pro Lys
            115                 120                 125

Gly Arg Lys Phe Lys Asp Phe Thr Ser Lys Phe Asn Ile Ala Ser Glu
130                 135                 140

Ala Lys Glu Asn Glu Pro Ile Ser Val Ile Gly Tyr Pro Asn Pro Asn
145                 150                 155                 160

Gly Asn Lys Leu Gln Met Tyr Glu Ser Thr Gly Lys Val Leu Ser Val
                165                 170                 175

Asn Gly Asn Ile Val Ser Ser Asp Ala Ile Ile Gln Pro Gly Ser Ser
            180                 185                 190

Gly Ser Pro Ile Leu Asn Ser Lys His Glu Ala Ile Gly Val Ile Tyr
            195                 200                 205

Ala Gly Asn Lys Pro Ser Gly Glu Ser Thr Arg Gly Phe Ala Val Tyr
210                 215                 220

Phe Ser Pro Glu Ile Lys Lys Phe Ile Ala Asp Asn Leu Asp Lys
225                 230                 235

<210> SEQ ID NO 26
<211> LENGTH: 470
<212> TYPE: PRT
<213> ORGANISM: Staphylococcus aureus

<400> SEQUENCE: 26

Met Gly Cys Thr Val Lys Met Asn Lys Ile Asn Asp Arg Asp Leu Thr
1               5                   10                  15

Glu Leu Ser Ser Tyr Trp Val Tyr Gln Asn Ile Asp Ile Lys Lys Glu
            20                  25                  30

Phe Lys Val Asn Gly Lys Arg Phe Lys Gln Val Asp Ser Tyr Asn Asp
            35                  40                  45

Asp Lys Asn Ser Asn Leu Asn Gly Ala Ala Asp Ile Lys Ile Tyr Glu
 50                  55                  60

Leu Leu Asp Asp Lys Ser Lys Pro Thr Gly Gln Gln Thr Ile Ile Tyr
 65                  70                  75                  80

Gln Gly Thr Ser Asn Glu Ala Ile Asn Pro Asn Asn Pro Leu Lys Ser
                85                  90                  95

Ser Gly Phe Gly Asp Asp Trp Leu Gln Asn Ala Lys Leu Met Asn Asn
            100                 105                 110

Asp Asn Glu Ser Thr Asp Tyr Leu Lys Gln Thr Asp Gln Leu Ser Asn
            115                 120                 125

Gln Tyr Lys Ile Lys Leu Glu Asp Ala Asp Arg Leu Ser Asn Ser Asp
130                 135                 140

Phe Leu Lys Lys Tyr Arg Met Glu Ser Ser Asn Phe Lys Asn Lys Thr
145                 150                 155                 160

Ile Val Ala Asp Gly Gly Asn Ser Glu Gly Ala Gly Ala Lys Tyr
                165                 170                 175
```

-continued

```
Gln Gly Ala Lys His Pro Asn Glu Lys Val Val Ala Thr Asp Ser Ala
            180                 185                 190

Met Ile Pro Tyr Ala Ala Trp Gln Lys Phe Ala Arg Pro Arg Phe Asp
        195                 200                 205

Asn Met Ile Ser Phe Asn Ser Thr Asn Asp Leu Leu Thr Trp Leu Gln
210                 215                 220

Asp Pro Phe Ile Lys Asp Met Pro Gly Lys Arg Val Asn Ile Asn Asp
225                 230                 235                 240

Gly Val Pro Arg Leu Asp Thr Leu Ile Asp Ser His Val Gly Tyr Lys
                245                 250                 255

Arg Lys Leu Asn Arg Lys Asp Asn Thr Tyr Asp Thr Val Pro Leu Ile
            260                 265                 270

Lys Ile Lys Ser Val Lys Asp Thr Glu Ile Lys Asn Gly Lys Lys Val
        275                 280                 285

Lys Lys Thr Ile Asn Ile Thr Leu Asp Met Asp Gly Arg Ile Pro Ile
290                 295                 300

Asn Val Trp Thr Gly Asp Ser Ile Ala Arg Ser Gly Arg Gly Thr Leu
305                 310                 315                 320

Ile Lys Leu Asn Leu Glu Asn Leu Asp Ala Leu Ser Lys Leu Ile Thr
                325                 330                 335

Gly Glu Thr Ser Gly Met Leu Ala Glu Cys Val Ile Phe Leu Asn Glu
            340                 345                 350

Ser Phe Asn Ile Ser Glu Asn Glu Lys Asn Phe Ala Asp Arg Lys
        355                 360                 365

Lys Gln Leu Ser Glu Gly Phe Lys Asp Lys Ile Asn Leu Phe Gln Leu
    370                 375                 380

Glu Glu Met Glu Arg Thr Leu Ile Ser Lys Ile Asn Ser Leu Glu Glu
385                 390                 395                 400

Val Ala Asp Glu Thr Ile Glu Ser Ile Ser Ala Val Lys His Leu Leu
                405                 410                 415

Pro Asp Phe Ala Leu Asp Ala Leu Lys Glu Arg Ile Asn Glu Leu Phe
            420                 425                 430

Lys Gly Ile Lys Ser Phe Ile Glu Lys Val Tyr Asp Ser Ile Asp Asn
        435                 440                 445

Glu Ile Leu Glu Ile Phe Lys Asn Ile Asp His Asp Phe Arg Asp Gly
    450                 455                 460

Val Ser Glu Glu Met Met
465                 470

<210> SEQ ID NO 27
<211> LENGTH: 306
<212> TYPE: PRT
<213> ORGANISM: Staphylococcus aureus

<400> SEQUENCE: 27

Met Lys Lys Lys Asp Gly Thr Gln Gln Phe Tyr His Tyr Ala Ser Ser
1               5                   10                  15

Val Lys Pro Ala Arg Val Ile Phe Thr Asp Ser Lys Pro Glu Ile Glu
            20                  25                  30

Leu Gly Leu Gln Ser Gly Gln Phe Trp Arg Lys Phe Glu Val Tyr Glu
        35                  40                  45

Gly Asp Lys Lys Leu Pro Ile Lys Leu Val Ser Tyr Asp Thr Val Lys
    50                  55                  60

Asp Tyr Ala Tyr Ile Arg Phe Ser Val Ser Asn Gly Thr Lys Ala Val
65                  70                  75                  80
```

```
Lys Ile Val Ser Ser Thr His Phe Asn Asn Lys Glu Glu Lys Tyr Asp
             85                  90                  95

Tyr Thr Leu Met Glu Phe Ala Gln Pro Ile Tyr Asn Ser Ala Asp Lys
            100                 105                 110

Phe Lys Thr Glu Glu Asp Tyr Lys Ala Glu Lys Leu Leu Ala Pro Tyr
        115                 120                 125

Lys Lys Ala Lys Thr Leu Glu Arg Gln Val Tyr Glu Leu Asn Lys Ile
    130                 135                 140

Gln Asp Lys Leu Pro Glu Lys Leu Lys Ala Glu Tyr Lys Lys Lys Leu
145                 150                 155                 160

Glu Asp Thr Lys Lys Ala Leu Asp Glu Gln Val Lys Ser Ala Ile Thr
                165                 170                 175

Glu Phe Gln Asn Val Gln Pro Thr Asn Glu Lys Met Thr Asp Leu Gln
            180                 185                 190

Asp Thr Lys Tyr Val Val Tyr Glu Ser Val Glu Asn Asn Glu Ser Met
        195                 200                 205

Met Asp Thr Phe Val Lys His Pro Ile Lys Thr Gly Met Leu Asn Gly
    210                 215                 220

Lys Lys Tyr Met Val Met Glu Thr Thr Asn Asp Asp Tyr Trp Lys Asp
225                 230                 235                 240

Phe Met Val Glu Gly Gln Arg Val Arg Thr Ile Ser Lys Asp Ala Lys
                245                 250                 255

Asn Asn Thr Arg Thr Ile Ile Phe Pro Tyr Val Glu Gly Lys Thr Leu
            260                 265                 270

Tyr Asp Ala Ile Val Lys Val His Val Lys Thr Ile Asp Tyr Asp Gly
        275                 280                 285

Gln Tyr His Val Arg Ile Val Asp Lys Glu Ala Phe Thr Lys Ala His
    290                 295                 300

Thr Asp
305

<210> SEQ ID NO 28
<211> LENGTH: 2659
<212> TYPE: PRT
<213> ORGANISM: Staphylococcus aureus

<400> SEQUENCE: 28

Asp Gln Thr Thr Ile Ile Asn Ser Leu Thr Phe Thr Glu Thr Val Pro
1               5                   10                  15

Asn Arg Ser Tyr Ala Arg Ala Ser Ala Asn Glu Ile Thr Ser Lys Thr
            20                  25                  30

Val Ser Asn Val Ser Arg Thr Gly Asn Asn Ala Asn Val Thr Val Thr
        35                  40                  45

Val Thr Tyr Gln Asp Gly Thr Thr Ser Thr Val Pro Val Lys
    50                  55                  60

His Val Ile Pro Glu Ile Val Ala His Ser His Tyr Thr Val Gln Gly
65                  70                  75                  80

Gln Asp Phe Pro Ala Gly Asn Gly Ser Ser Ala Ser Asp Tyr Phe Lys
                85                  90                  95

Leu Ser Asn Gly Ser Asp Ile Ala Asp Ala Thr Ile Thr Trp Val Ser
            100                 105                 110

Gly Gln Ala Pro Asn Lys Asp Asn Thr Arg Ile Gly Glu Asp Ile Thr
        115                 120                 125

Val Thr Ala His Ile Leu Ile Asp Gly Glu Thr Thr Pro Ile Thr Lys
    130                 135                 140
```

-continued

```
Thr Ala Thr Tyr Lys Val Val Arg Thr Val Pro Lys His Val Phe Glu
145                 150                 155                 160

Thr Ala Arg Gly Val Leu Tyr Pro Gly Val Ser Asp Met Tyr Asp Ala
            165                 170                 175

Lys Gln Tyr Val Lys Pro Val Asn Asn Ser Trp Ser Thr Asn Ala Gln
        180                 185                 190

His Met Asn Phe Gln Phe Val Gly Thr Tyr Gly Pro Asn Lys Asp Val
    195                 200                 205

Val Gly Ile Ser Thr Arg Leu Ile Arg Val Thr Tyr Asp Asn Arg Gln
210                 215                 220

Thr Glu Asp Leu Thr Ile Leu Ser Lys Val Lys Pro Pro Arg
225                 230                 235                 240

Ile Asp Ala Asn Ser Val Thr Tyr Lys Ala Gly Leu Thr Asn Gln Glu
                245                 250                 255

Ile Lys Val Asn Asn Val Leu Asn Asn Ser Ser Val Lys Leu Phe Lys
            260                 265                 270

Ala Asp Asn Thr Pro Leu Asn Val Thr Asn Ile Thr His Gly Ser Gly
        275                 280                 285

Phe Ser Ser Val Val Thr Val Ser Asp Ala Leu Pro Asn Gly Gly Ile
    290                 295                 300

Lys Ala Lys Ser Ser Ile Ser Met Asn Asn Val Thr Tyr Thr Thr Gln
305                 310                 315                 320

Asp Glu His Gly Gln Val Val Thr Val Thr Arg Asn Glu Ser Val Asp
                325                 330                 335

Ser Asn Asp Ser Ala Thr Val Thr Val Thr Pro Gln Leu Gln Ala Thr
            340                 345                 350

Thr Glu Gly Ala Val Phe Ile Lys Gly Gly Asp Gly Phe Asp Phe Gly
        355                 360                 365

His Val Glu Arg Phe Ile Gln Asn Pro Pro His Gly Ala Thr Val Ala
    370                 375                 380

Trp His Asp Ser Pro Asp Thr Trp Lys Asn Thr Val Gly Asn Thr His
385                 390                 395                 400

Lys Thr Ala Val Val Thr Leu Pro Asn Gly Gln Gly Thr Arg Asn Val
                405                 410                 415

Glu Val Pro Val Lys Val Tyr Pro Val Ala Asn Ala Lys Ala Pro Ser
            420                 425                 430

Arg Asp Val Lys Gly Gln Asn Leu Thr Asn Gly Thr Asp Ala Met Asn
        435                 440                 445

Tyr Ile Thr Phe Asp Pro Asn Thr Asn Thr Asn Gly Ile Thr Ala Ala
    450                 455                 460

Trp Ala Asn Arg Gln Gln Pro Asn Asn Gln Gln Ala Gly Val Gln His
465                 470                 475                 480

Leu Asn Val Asp Val Thr Tyr Pro Gly Ile Ser Ala Ala Lys Arg Val
                485                 490                 495

Pro Val Thr Val Asn Val Tyr Gln Phe Glu Phe Pro Gln Thr Thr Tyr
            500                 505                 510

Thr Thr Thr Val Gly Gly Thr Leu Ala Ser Gly Thr Gln Ala Ser Gly
        515                 520                 525

Tyr Ala His Met Gln Asn Ala Thr Gly Leu Pro Thr Asp Gly Phe Thr
    530                 535                 540

Tyr Lys Trp Asn Arg Asp Thr Thr Gly Thr Asn Asp Ala Asn Trp Ser
545                 550                 555                 560

Ala Met Asn Lys Pro Asn Val Ala Lys Val Val Asn Ala Lys Tyr Asp
                565                 570                 575
```

```
Val Ile Tyr Asn Gly His Thr Phe Ala Thr Ser Leu Pro Ala Lys Phe
            580                 585                 590

Val Val Lys Asp Val Gln Pro Ala Lys Pro Thr Val Thr Glu Thr Ala
            595                 600                 605

Ala Gly Ala Ile Thr Ile Ala Pro Gly Ala Asn Gln Thr Val Asn Thr
        610                 615                 620

His Ala Gly Asn Val Thr Thr Tyr Ala Asp Lys Leu Val Ile Lys Arg
625                 630                 635                 640

Asn Gly Asn Val Val Thr Thr Phe Thr Arg Arg Asn Asn Thr Ser Pro
                645                 650                 655

Trp Val Lys Glu Ala Ser Ala Ala Thr Val Ala Gly Ile Ala Gly Thr
            660                 665                 670

Asn Asn Gly Ile Thr Val Ala Ala Gly Thr Phe Asn Pro Ala Asp Thr
            675                 680                 685

Ile Gln Val Val Ala Thr Gln Gly Ser Gly Glu Thr Val Ser Asp Glu
        690                 695                 700

Gln Arg Ser Asp Asp Phe Thr Val Val Ala Pro Gln Pro Asn Gln Ala
705                 710                 715                 720

Thr Thr Lys Ile Trp Gln Asn Gly His Ile Asp Ile Thr Pro Asn Asn
                725                 730                 735

Pro Ser Gly His Leu Ile Asn Pro Thr Gln Ala Met Asp Ile Ala Tyr
            740                 745                 750

Thr Glu Lys Val Gly Asn Gly Ala Glu His Ser Lys Thr Ile Asn Val
            755                 760                 765

Val Arg Gly Gln Asn Asn Gln Trp Thr Ile Ala Asn Lys Pro Asp Tyr
            770                 775                 780

Val Thr Leu Asp Ala Gln Thr Gly Lys Val Thr Phe Asn Ala Asn Thr
785                 790                 795                 800

Ile Lys Pro Asn Ser Ser Ile Thr Ile Thr Pro Lys Ala Gly Thr Gly
                805                 810                 815

His Ser Val Ser Ser Asn Pro Ser Thr Leu Thr Ala Pro Ala Ala His
            820                 825                 830

Thr Val Asn Thr Thr Glu Ile Val Lys Asp Tyr Gly Ser Asn Val Thr
            835                 840                 845

Ala Ala Glu Ile Asn Asn Ala Val Gln Val Ala Asn Lys Arg Thr Ala
        850                 855                 860

Thr Ile Lys Asn Gly Thr Ala Met Pro Thr Asn Leu Ala Gly Gly Ser
865                 870                 875                 880

Thr Thr Thr Ile Pro Val Thr Val Thr Tyr Asn Asp Gly Ser Thr Glu
                885                 890                 895

Glu Val Gln Glu Ser Ile Phe Thr Lys Ala Asp Lys Arg Glu Leu Ile
            900                 905                 910

Thr Ala Lys Asn His Leu Asp Asp Pro Val Ser Thr Glu Gly Lys Lys
            915                 920                 925

Pro Gly Thr Ile Thr Gln Tyr Asn Asn Ala Met His Asn Ala Gln Gln
        930                 935                 940

Gln Ile Asn Thr Ala Lys Thr Glu Ala Gln Gln Val Ile Asn Asn Glu
945                 950                 955                 960

Arg Ala Thr Pro Gln Gln Val Ser Asp Ala Leu Thr Lys Val Arg Ala
                965                 970                 975

Ala Gln Thr Lys Ile Asp Gln Ala Lys Ala Leu Leu Gln Asn Lys Glu
            980                 985                 990

Asp Asn Ser Gln Leu Val Thr Ser  Lys Asn Asn Leu Gln  Ser Ser Val
```

-continued

```
                995                 1000                1005
Asn Gln  Val Pro Ser Thr  Ala Gly Met  Thr Gln Gln  Ser Ile Asp
    1010                 1015                 1020

Asn Tyr  Asn Ala Lys Lys  Arg Glu Ala  Glu Thr Glu  Ile Thr Ala
    1025                 1030                 1035

Ala Gln  Arg Val Ile Asp  Asn Gly Asp  Ala Thr Ala  Gln Gln Ile
    1040                 1045                 1050

Ser Asp  Glu Lys His Arg  Val Asp Asn  Ala Leu Thr  Ala Leu Asn
    1055                 1060                 1065

Gln Ala  Lys His Asp Leu  Thr Ala Asp  Thr His Ala  Leu Glu Gln
    1070                 1075                 1080

Ala Val  Gln Gln Leu Asn  Arg Thr Gly  Thr Thr Gly  Lys Lys
    1085                 1090                 1095

Pro Ala  Ser Ile Thr Ala  Tyr Asn Asn  Ser Ile Arg  Ala Leu Gln
    1100                 1105                 1110

Ser Asp  Leu Thr Ser Ala  Lys Asn Ser  Ala Asn Ala  Ile Ile Gln
    1115                 1120                 1125

Lys Pro  Ile Arg Thr Val  Gln Glu Val  Gln Ser Ala  Leu Thr Asn
    1130                 1135                 1140

Val Asn  Arg Val Asn Glu  Arg Leu Thr  Gln Ala Ile  Asn Gln Leu
    1145                 1150                 1155

Val Pro  Leu Ala Asp Asn  Ser Ala Leu  Lys Thr Ala  Lys Thr Lys
    1160                 1165                 1170

Leu Asp  Glu Glu Ile Asn  Lys Ser Val  Thr Thr Asp  Gly Met Thr
    1175                 1180                 1185

Gln Ser  Ser Ile Gln Ala  Tyr Glu Asn  Ala Lys Arg  Ala Gly Gln
    1190                 1195                 1200

Thr Glu  Ser Thr Asn Ala  Gln Asn Val  Ile Asn Asn  Gly Asp Ala
    1205                 1210                 1215

Thr Asp  Gln Gln Ile Ala  Ala Glu Lys  Thr Lys Val  Glu Glu Lys
    1220                 1225                 1230

Tyr Asn  Ser Leu Lys Gln  Ala Ile Ala  Gly Leu Thr  Pro Asp Leu
    1235                 1240                 1245

Ala Pro  Leu Gln Thr Ala  Lys Thr Gln  Leu Gln Asn  Asp Ile Asp
    1250                 1255                 1260

Gln Pro  Thr Ser Thr Thr  Gly Met Thr  Ser Ala Ser  Ile Ala Ala
    1265                 1270                 1275

Phe Asn  Glu Lys Leu Ser  Ala Ala Arg  Thr Lys Ile  Gln Glu Ile
    1280                 1285                 1290

Asp Arg  Val Leu Ala Ser  His Pro Asp  Val Ala Thr  Ile Arg Gln
    1295                 1300                 1305

Asn Val  Thr Ala Ala Asn  Ala Ala Lys  Ser Ala Leu  Asp Gln Ala
    1310                 1315                 1320

Arg Asn  Gly Leu Thr Val  Asp Lys Ala  Pro Leu Glu  Asn Ala Lys
    1325                 1330                 1335

Asn Gln  Leu Gln Tyr Ser  Ile Asp Thr  Gln Thr Ser  Thr Thr Gly
    1340                 1345                 1350

Met Thr  Gln Asp Ser Ile  Asn Ala Tyr  Asn Ala Lys  Leu Thr Ala
    1355                 1360                 1365

Ala Arg  Asn Lys Ile Gln  Gln Ile Asn  Gln Val Leu  Ala Gly Ser
    1370                 1375                 1380

Pro Thr  Val Glu Gln Ile  Asn Thr Asn  Thr Ser Thr  Ala Asn Gln
    1385                 1390                 1395
```

-continued

```
Ala Lys Ser Asp Leu Asp His Ala Arg Gln Ala Leu Thr Pro Asp
    1400                1405                1410

Lys Ala Pro Leu Gln Thr Ala Lys Thr Gln Leu Glu Gln Ser Ile
    1415                1420                1425

Asn Gln Pro Thr Asp Thr Thr Gly Met Thr Thr Ala Ser Leu Asn
    1430                1435                1440

Ala Tyr Asn Gln Lys Leu Gln Ala Ala Arg Gln Lys Leu Thr Glu
    1445                1450                1455

Ile Asn Gln Val Leu Asn Gly Asn Pro Thr Val Gln Asn Ile Asn
    1460                1465                1470

Asp Lys Val Thr Glu Ala Asn Gln Ala Lys Asp Gln Leu Asn Thr
    1475                1480                1485

Ala Arg Gln Gly Leu Thr Leu Asp Arg Gln Pro Ala Leu Thr Thr
    1490                1495                1500

Leu His Gly Ala Ser Asn Leu Asn Gln Ala Gln Gln Asn Asn Phe
    1505                1510                1515

Thr Gln Gln Ile Asn Ala Ala Gln Asn His Ala Ala Leu Glu Thr
    1520                1525                1530

Ile Lys Ser Asn Ile Thr Ala Leu Asn Thr Ala Met Thr Lys Leu
    1535                1540                1545

Lys Asp Ser Val Ala Asp Asn Asn Thr Ile Lys Ser Asp Gln Asn
    1550                1555                1560

Tyr Thr Asp Ala Thr Pro Ala Asn Lys Gln Ala Tyr Asp Asn Ala
    1565                1570                1575

Val Asn Ala Ala Lys Gly Val Ile Gly Glu Thr Thr Asn Pro Thr
    1580                1585                1590

Met Asp Val Asn Thr Val Asn Gln Lys Ala Ala Ser Val Lys Ser
    1595                1600                1605

Thr Lys Asp Ala Leu Asp Gly Gln Gln Asn Leu Gln Arg Ala Lys
    1610                1615                1620

Thr Glu Ala Thr Asn Ala Ile Thr His Ala Ser Asp Leu Asn Gln
    1625                1630                1635

Ala Gln Lys Asn Ala Leu Thr Gln Gln Val Asn Ser Ala Gln Asn
    1640                1645                1650

Val Gln Ala Val Asn Asp Ile Lys Gln Thr Thr Gln Ser Leu Asn
    1655                1660                1665

Thr Ala Met Thr Gly Leu Lys Arg Gly Val Ala Asn His Asn Gln
    1670                1675                1680

Val Val Gln Ser Asp Asn Tyr Val Asn Ala Asp Thr Asn Lys Lys
    1685                1690                1695

Asn Asp Tyr Asn Asn Ala Tyr Asn His Ala Asn Asp Ile Ile Asn
    1700                1705                1710

Gly Asn Ala Gln His Pro Val Ile Thr Pro Ser Asp Val Asn Asn
    1715                1720                1725

Ala Leu Ser Asn Val Thr Ser Lys Glu His Ala Leu Asn Gly Glu
    1730                1735                1740

Ala Lys Leu Asn Ala Ala Lys Gln Glu Ala Asn Thr Ala Leu Gly
    1745                1750                1755

His Leu Asn Asn Leu Asn Asn Ala Gln Arg Gln Asn Leu Gln Ser
    1760                1765                1770

Gln Ile Asn Gly Ala His Gln Ile Asp Ala Val Asn Thr Ile Lys
    1775                1780                1785

Gln Asn Ala Thr Asn Leu Asn Ser Ala Met Gly Asn Leu Arg Gln
    1790                1795                1800
```

-continued

```
Ala Val Ala Asp Lys Asp Gln Val Lys Arg Thr Glu Asp Tyr Ala
1805                1810                1815

Asp Ala Asp Thr Ala Lys Gln Asn Ala Tyr Asn Ser Ala Val Ser
1820                1825                1830

Ser Ala Glu Thr Ile Ile Asn Gln Thr Thr Asn Pro Thr Met Ser
1835                1840                1845

Val Asp Asp Val Asn Arg Ala Thr Ser Ala Val Thr Ser Asn Lys
1850                1855                1860

Asn Ala Leu Asn Gly Tyr Glu Lys Leu Ala Gln Ser Lys Thr Asp
1865                1870                1875

Ala Ala Arg Ala Ile Asp Ala Leu Pro His Leu Asn Asn Ala Gln
1880                1885                1890

Lys Ala Asp Val Lys Ser Lys Ile Asn Ala Ala Ser Asn Ile Ala
1895                1900                1905

Gly Val Asn Thr Val Lys Gln Gln Gly Thr Asp Leu Asn Thr Ala
1910                1915                1920

Met Gly Asn Leu Gln Gly Ala Ile Asn Asp Glu Gln Thr Thr Leu
1925                1930                1935

Asn Ser Gln Asn Tyr Gln Asp Ala Thr Pro Ser Lys Lys Thr Ala
1940                1945                1950

Tyr Thr Asn Ala Val Gln Ala Ala Lys Asp Ile Leu Asn Lys Ser
1955                1960                1965

Asn Gly Gln Asn Lys Thr Lys Asp Gln Val Thr Glu Ala Met Asn
1970                1975                1980

Gln Val Asn Ser Ala Lys Asn Asn Leu Asp Gly Thr Arg Leu Leu
1985                1990                1995

Asp Gln Ala Lys Gln Thr Ala Lys Gln Gln Leu Asn Asn Met Thr
2000                2005                2010

His Leu Thr Thr Ala Gln Lys Thr Asn Leu Thr Asn Gln Ile Asn
2015                2020                2025

Ser Gly Thr Thr Val Ala Gly Val Gln Thr Val Gln Ser Asn Ala
2030                2035                2040

Asn Thr Leu Asp Gln Ala Met Asn Thr Leu Arg Gln Ser Ile Ala
2045                2050                2055

Asn Lys Asp Ala Thr Lys Ala Ser Glu Asp Tyr Val Asp Ala Asn
2060                2065                2070

Asn Asp Lys Gln Thr Ala Tyr Asn Asn Ala Val Ala Ala Ala Glu
2075                2080                2085

Thr Ile Ile Asn Ala Asn Ser Asn Pro Glu Met Asn Pro Ser Thr
2090                2095                2100

Ile Thr Gln Lys Ala Glu Gln Val Asn Ser Ser Lys Thr Ala Leu
2105                2110                2115

Asn Gly Asp Glu Asn Leu Ala Ala Ala Lys Gln Asn Ala Lys Thr
2120                2125                2130

Tyr Leu Asn Thr Leu Thr Ser Ile Thr Asp Ala Gln Lys Asn Asn
2135                2140                2145

Leu Ile Ser Gln Ile Thr Ser Ala Thr Arg Val Ser Gly Val Asp
2150                2155                2160

Thr Val Lys Gln Asn Ala Gln His Leu Asp Gln Ala Met Ala Ser
2165                2170                2175

Leu Gln Asn Gly Ile Asn Asn Glu Ser Gln Val Lys Ser Ser Glu
2180                2185                2190

Lys Tyr Arg Asp Ala Asp Thr Asn Lys Gln Gln Glu Tyr Asp Asn
```

-continued

```
            2195                2200                2205

Ala Ile Thr Ala Ala Lys Ala Ile Leu Asn Lys Ser Thr Gly Pro
2210                2215                2220

Asn Thr Ala Gln Asn Ala Val Glu Ala Ala Leu Gln Arg Val Asn
2225                2230                2235

Asn Ala Lys Asp Ala Leu Asn Gly Asp Ala Lys Leu Ile Ala Ala
2240                2245                2250

Gln Asn Ala Ala Lys Gln His Leu Gly Thr Leu Thr His Ile Thr
2255                2260                2265

Thr Ala Gln Arg Asn Asp Leu Thr Asn Gln Ile Ser Gln Ala Thr
2270                2275                2280

Asn Leu Ala Gly Val Glu Ser Val Lys Gln Asn Ala Asn Ser Leu
2285                2290                2295

Asp Gly Ala Met Gly Asn Leu Gln Thr Ala Ile Asn Asp Lys Ser
2300                2305                2310

Gly Thr Leu Ala Ser Gln Asn Phe Leu Asp Ala Asp Glu Gln Lys
2315                2320                2325

Arg Asn Ala Tyr Asn Gln Ala Val Ser Ala Ala Glu Thr Ile Leu
2330                2335                2340

Asn Lys Gln Thr Gly Pro Asn Thr Ala Lys Thr Ala Val Glu Gln
2345                2350                2355

Ala Leu Asn Asn Val Asn Asn Ala Lys His Ala Leu Asn Gly Thr
2360                2365                2370

Gln Asn Leu Asn Asn Ala Lys Gln Ala Ala Ile Thr Ala Ile Asn
2375                2380                2385

Gly Ala Ser Asp Leu Asn Gln Lys Gln Lys Asp Ala Leu Lys Ala
2390                2395                2400

Gln Ala Asn Gly Ala Gln Arg Val Ser Asn Ala Gln Asp Val Gln
2405                2410                2415

His Asn Ala Thr Glu Leu Asn Thr Ala Met Gly Thr Leu Lys His
2420                2425                2430

Ala Ile Ala Asp Lys Thr Asn Thr Leu Ala Ser Ser Lys Tyr Val
2435                2440                2445

Asn Ala Asp Ser Thr Lys Gln Asn Ala Tyr Thr Thr Lys Val Thr
2450                2455                2460

Asn Ala Glu His Ile Ile Ser Gly Thr Pro Thr Val Val Thr Thr
2465                2470                2475

Pro Ser Glu Val Thr Ala Ala Asn Gln Val Asn Ser Ala Lys
2480                2485                2490

Gln Glu Leu Asn Gly Asp Glu Arg Leu Arg Glu Ala Lys Gln Asn
2495                2500                2505

Ala Asn Thr Ala Ile Asp Ala Leu Thr Gln Leu Asn Thr Pro Gln
2510                2515                2520

Lys Ala Lys Leu Lys Glu Gln Val Gly Gln Ala Asn Arg Leu Glu
2525                2530                2535

Asp Val Gln Thr Val Gln Thr Asn Gly Gln Ala Leu Asn Asn Ala
2540                2545                2550

Met Lys Gly Leu Arg Asp Ser Ile Ala Asn Glu Thr Thr Val Lys
2555                2560                2565

Thr Ser Gln Asn Tyr Thr Asp Ala Ser Pro Asn Asn Gln Ser Thr
2570                2575                2580

Tyr Asn Ser Ala Val Ser Asn Ala Lys Gly Ile Ile Asn Gln Thr
2585                2590                2595
```

```
Asn Asn Pro Thr Met Asp Thr  Ser Ala Ile Thr Gln  Ala Thr Thr
    2600            2605                2610

Gln Val  Asn Asn Ala Lys Asn  Gly Leu Asn Gly Ala  Glu Asn Leu
    2615            2620                2625

Arg Asn  Ala Gln Asn Thr Ala  Lys Gln Asn Leu Asn  Thr Leu Ser
    2630            2635                2640

His Leu  Thr Asn Asn Gln Lys  Ser Ala Ile Ser Ser  Gln Ile Asp
    2645            2650                2655

Arg

<210> SEQ ID NO 29
<211> LENGTH: 496
<212> TYPE: PRT
<213> ORGANISM: Staphylococcus aureus

<400> SEQUENCE: 29

Met Asn Met Lys Lys Lys Glu Lys His Ala Ile Arg Lys Lys Ser Ile
1               5                   10                  15

Gly Val Ala Ser Val Leu Val Gly Thr Leu Ile Gly Phe Gly Leu Leu
            20                  25                  30

Ser Ser Lys Glu Ala Asp Ala Ser Glu Asn Ser Val Thr Gln Ser Asp
        35                  40                  45

Ser Ala Ser Asn Glu Ser Lys Ser Asn Asp Ser Ser Val Ser Ala
    50                  55                  60

Ala Pro Lys Thr Asp Asp Thr Asn Val Ser Asp Thr Lys Thr Ser Ser
65                  70                  75                  80

Asn Thr Asn Asn Gly Glu Thr Ser Val Ala Gln Asn Pro Ala Gln Gln
                85                  90                  95

Glu Thr Thr Gln Ser Ser Thr Asn Ala Thr Glu Glu Thr Pro
            100                 105                 110

Val Thr Gly Glu Ala Thr Thr Thr Thr Asn Gln Ala Asn Thr Pro
        115                 120                 125

Ala Thr Thr Gln Ser Ser Asn Thr Asn Ala Glu Glu Leu Val Asn Gln
    130                 135                 140

Thr Ser Asn Glu Thr Thr Phe Asn Asp Thr Asn Thr Val Ser Ser Val
145                 150                 155                 160

Asn Ser Pro Gln Asn Ser Thr Asn Ala Glu Asn Val Ser Thr Thr Gln
                165                 170                 175

Asp Thr Ser Thr Glu Ala Thr Pro Ser Asn Asn Glu Ser Ala Pro Gln
            180                 185                 190

Ser Thr Asp Ala Ser Asn Lys Asp Val Val Asn Gln Ala Val Asn Thr
        195                 200                 205

Ser Ala Pro Arg Met Arg Ala Phe Ser Leu Ala Ala Val Ala Ala Asp
    210                 215                 220

Ala Pro Ala Ala Gly Thr Asp Ile Thr Asn Gln Leu Thr Asn Val Thr
225                 230                 235                 240

Val Gly Ile Asp Ser Gly Thr Thr Val Tyr Pro His Gln Ala Gly Tyr
                245                 250                 255

Val Lys Leu Asn Tyr Gly Phe Ser Val Pro Asn Ser Ala Val Lys Gly
            260                 265                 270

Asp Thr Phe Lys Ile Thr Val Pro Lys Glu Leu Asn Leu Asn Gly Val
        275                 280                 285

Thr Ser Thr Ala Lys Val Pro Pro Ile Met Ala Gly Asp Gln Val Leu
    290                 295                 300

Ala Asn Gly Val Ile Asp Ser Asp Gly Asn Val Ile Tyr Thr Phe Thr
```

```
                  305                 310                 315                 320
Asp Tyr Val Asn Thr Lys Asp Val Lys Ala Thr Leu Thr Met Pro
                325                 330                 335

Ala Tyr Ile Asp Pro Glu Asn Val Lys Lys Thr Gly Asn Val Thr Leu
                340                 345                 350

Ala Thr Gly Ile Gly Ser Thr Thr Ala Asn Lys Thr Val Leu Val Asp
                355                 360                 365

Tyr Glu Lys Tyr Gly Lys Phe Tyr Asn Leu Ser Ile Lys Gly Thr Ile
            370                 375                 380

Asp Gln Ile Asp Lys Thr Asn Asn Thr Tyr Arg Gln Thr Ile Tyr Val
385                 390                 395                 400

Asn Pro Ser Gly Asp Asn Val Ile Ala Pro Val Leu Thr Gly Asn Leu
                405                 410                 415

Lys Pro Asn Thr Asp Ser Asn Ala Leu Ile Asp Gln Asn Thr Ser
                420                 425                 430

Ile Lys Val Tyr Lys Val Asp Asn Ala Ala Asp Leu Ser Glu Ser Tyr
            435                 440                 445

Phe Val Asn Pro Glu Asn Phe Glu Asp Val Thr Asn Ser Val Asn Ile
        450                 455                 460

Thr Phe Pro Asn Pro Asn Gln Tyr Lys Val Glu Phe Asn Thr Pro Asp
465                 470                 475                 480

Asp Gln Ile Thr Thr Pro Tyr Ile Val Val Asn Gly His Ile Asp
                485                 490                 495

<210> SEQ ID NO 30
<211> LENGTH: 541
<212> TYPE: PRT
<213> ORGANISM: Staphylococcus aureus

<400> SEQUENCE: 30

Asp Gln Tyr Leu Leu Glu Arg Lys Lys Ser Gln Tyr Glu Asp Tyr Lys
1               5                   10                  15

Gln Trp Tyr Ala Asn Tyr Lys Lys Glu Asn Pro Arg Thr Asp Leu Lys
                20                  25                  30

Met Ala Asn Phe His Lys Tyr Asn Leu Glu Glu Leu Ser Met Lys Glu
            35                  40                  45

Tyr Asn Glu Leu Gln Asp Ala Leu Lys Arg Ala Leu Asp Asp Phe His
        50                  55                  60

Arg Glu Val Lys Asp Ile Lys Asp Lys Asn Ser Asp Leu Lys Thr Phe
65              70                  75                  80

Asn Ala Ala Glu Glu Asp Lys Ala Thr Lys Glu Val Tyr Asp Leu Val
                85                  90                  95

Ser Glu Ile Asp Thr Leu Val Val Ser Tyr Tyr Gly Asp Lys Asp Tyr
            100                 105                 110

Gly Glu His Ala Lys Glu Leu Arg Ala Lys Leu Asp Leu Ile Leu Gly
        115                 120                 125

Asp Thr Asp Asn Pro His Lys Ile Thr Asn Glu Arg Ile Lys Lys Glu
130                 135                 140

Met Ile Asp Asp Leu Asn Ser Ile Ile Asp Asp Phe Phe Met Glu Thr
145                 150                 155                 160

Lys Gln Asn Arg Pro Lys Ser Ile Thr Lys Tyr Asn Pro Thr Thr His
                165                 170                 175

Asn Tyr Lys Thr Asn Ser Asp Asn Lys Pro Asn Phe Asp Lys Leu Val
            180                 185                 190

Glu Glu Thr Lys Lys Ala Val Lys Glu Ala Asp Asp Ser Trp Lys Lys
```

```
                195                 200                 205
Lys Thr Val Lys Lys Tyr Gly Glu Thr Glu Thr Lys Ser Pro Val Val
210                 215                 220

Lys Glu Glu Lys Val Glu Pro Gln Ala Pro Lys Val Asp Asn
225                 230                 235                 240

Gln Gln Glu Val Lys Thr Thr Ala Gly Lys Ala Glu Thr Thr Gln
                    245                 250                 255

Pro Val Ala Gln Pro Leu Val Lys Ile Pro Gln Gly Thr Ile Thr Gly
                260                 265                 270

Glu Ile Val Lys Gly Pro Glu Tyr Pro Thr Met Glu Asn Lys Thr Val
                275                 280                 285

Gln Gly Glu Ile Val Gln Gly Pro Asp Phe Leu Thr Met Glu Gln Ser
                290                 295                 300

Gly Pro Ser Leu Ser Asn Asn Tyr Thr Asn Pro Leu Thr Asn Pro
305                 310                 315                 320

Ile Leu Glu Gly Leu Glu Gly Ser Ser Lys Leu Glu Ile Lys Pro
                325                 330                 335

Gln Gly Thr Glu Ser Thr Leu Lys Gly Thr Gln Gly Glu Ser Ser Asp
                340                 345                 350

Ile Glu Val Lys Pro Gln Ala Thr Glu Thr Thr Glu Ala Ser Gln Tyr
                355                 360                 365

Gly Pro Arg Pro Gln Phe Asn Lys Thr Pro Lys Tyr Val Lys Tyr Arg
                370                 375                 380

Asp Ala Gly Thr Gly Ile Arg Glu Tyr Asn Asp Gly Thr Phe Gly Tyr
385                 390                 395                 400

Glu Ala Arg Pro Arg Phe Asn Lys Pro Ser Glu Thr Asn Ala Tyr Asn
                405                 410                 415

Val Thr Thr His Ala Asn Gly Gln Val Ser Tyr Gly Ala Arg Pro Thr
                420                 425                 430

Tyr Lys Lys Pro Ser Glu Thr Asn Ala Tyr Asn Val Thr Thr His Ala
                435                 440                 445

Asn Gly Gln Val Ser Tyr Gly Ala Arg Pro Thr Gln Asn Lys Pro Ser
450                 455                 460

Lys Thr Asn Ala Tyr Asn Val Thr Thr His Gly Asn Gly Gln Val Ser
465                 470                 475                 480

Tyr Gly Ala Arg Gln Ala Gln Asn Lys Pro Ser Lys Thr Asn Ala Tyr
                485                 490                 495

Asn Val Thr Thr His Ala Asn Gly Gln Val Ser Tyr Gly Ala Arg Pro
                500                 505                 510

Thr Tyr Lys Lys Pro Ser Lys Thr Asn Ala Tyr Asn Val Thr Thr His
                515                 520                 525

Ala Asp Gly Thr Ala Thr Tyr Gly Pro Arg Val Thr Lys
530                 535                 540

<210> SEQ ID NO 31
<211> LENGTH: 356
<212> TYPE: PRT
<213> ORGANISM: Staphylococcus aureus

<400> SEQUENCE: 31

Met Lys Met Arg Thr Ile Ala Lys Thr Ser Leu Ala Leu Gly Leu Leu
1               5                   10                  15

Thr Thr Gly Ala Ile Thr Val Thr Gln Ser Val Lys Ala Glu Lys
                20                  25                  30

Ile Gln Ser Thr Lys Val Asp Lys Val Pro Thr Leu Lys Ala Glu Arg
```

```
                35                  40                  45
Leu Ala Met Ile Asn Ile Thr Ala Gly Ala Asn Ser Ala Thr Thr Gln
 50                  55                  60

Ala Ala Asn Thr Arg Gln Glu Arg Thr Pro Lys Leu Glu Lys Ala Pro
 65                  70                  75                  80

Asn Thr Asn Glu Glu Lys Thr Ser Ala Ser Lys Ile Glu Lys Ile Ser
                85                  90                  95

Gln Pro Lys Gln Glu Gln Lys Thr Leu Asn Ile Ser Ala Thr Pro
                100                 105                 110

Ala Pro Lys Gln Glu Gln Ser Gln Thr Thr Glu Ser Thr Thr Pro
                115                 120                 125

Lys Thr Lys Val Thr Thr Pro Pro Ser Thr Asn Thr Pro Gln Pro Met
130                 135                 140

Gln Ser Thr Lys Ser Asp Thr Pro Gln Ser Pro Thr Ile Lys Gln Ala
145                 150                 155                 160

Gln Thr Asp Met Thr Pro Lys Tyr Glu Asp Leu Arg Ala Tyr Tyr Thr
                165                 170                 175

Lys Pro Ser Phe Glu Phe Glu Lys Gln Phe Gly Phe Met Leu Lys Pro
                180                 185                 190

Trp Thr Thr Val Arg Phe Met Asn Val Ile Pro Asn Arg Phe Ile Tyr
                195                 200                 205

Lys Ile Ala Leu Val Gly Lys Asp Glu Lys Tyr Lys Asp Gly Pro
210                 215                 220

Tyr Asp Asn Ile Asp Val Phe Ile Val Leu Glu Asp Asn Lys Tyr Gln
225                 230                 235                 240

Leu Lys Lys Tyr Ser Val Gly Gly Ile Thr Lys Thr Asn Ser Lys Lys
                245                 250                 255

Val Asn His Lys Val Glu Leu Ser Ile Thr Lys Lys Asp Asn Gln Gly
                260                 265                 270

Met Ile Ser Arg Asp Val Ser Glu Tyr Met Ile Thr Lys Glu Glu Ile
                275                 280                 285

Ser Leu Lys Glu Leu Asp Phe Lys Leu Arg Lys Gln Leu Ile Glu Lys
290                 295                 300

His Asn Leu Tyr Gly Asn Met Gly Ser Gly Thr Ile Val Ile Lys Met
305                 310                 315                 320

Lys Asn Gly Gly Lys Tyr Thr Phe Glu Leu His Lys Lys Leu Gln Glu
                325                 330                 335

His Arg Met Ala Asp Val Ile Asp Gly Thr Asn Ile Asp Asn Ile Glu
                340                 345                 350

Val Asn Ile Lys
        355

<210> SEQ ID NO 32
<211> LENGTH: 313
<212> TYPE: PRT
<213> ORGANISM: Staphylococcus aureus

<400> SEQUENCE: 32

Met Glu His Thr Thr Met Lys Ile Thr Thr Ile Ala Lys Thr Ser Leu
 1               5                  10                  15

Ala Leu Gly Leu Leu Thr Thr Gly Val Ile Thr Thr Thr Gln Ala
                20                  25                  30

Ala Asn Ala Thr Thr Leu Ser Ser Thr Lys Val Glu Ala Pro Gln Ser
                35                  40                  45

Thr Pro Pro Ser Thr Lys Ile Glu Ala Pro Gln Ser Lys Pro Asn Ala
```

```
                    50                  55                  60
Thr Thr Pro Pro Ser Thr Lys Val Glu Ala Pro Gln Gln Thr Ala Asn
 65                  70                  75                  80

Ala Thr Thr Pro Pro Ser Thr Lys Val Thr Thr Pro Pro Ser Thr Asn
                     85                  90                  95

Thr Pro Gln Pro Met Gln Ser Thr Lys Ser Asp Thr Pro Gln Ser Pro
                100                 105                 110

Thr Thr Lys Gln Val Pro Thr Glu Ile Asn Pro Lys Phe Lys Asp Leu
            115                 120                 125

Arg Ala Tyr Tyr Thr Lys Pro Ser Leu Glu Phe Lys Asn Glu Ile Gly
            130                 135                 140

Ile Ile Leu Lys Lys Trp Thr Thr Ile Arg Phe Met Asn Val Val Pro
145                 150                 155                 160

Asp Tyr Phe Ile Tyr Lys Ile Ala Leu Val Gly Lys Asp Asp Lys Lys
                165                 170                 175

Tyr Gly Glu Gly Val His Arg Asn Val Asp Val Phe Val Val Leu Glu
                180                 185                 190

Glu Asn Asn Tyr Asn Leu Glu Lys Tyr Ser Val Gly Gly Ile Thr Lys
            195                 200                 205

Ser Asn Ser Lys Lys Val Asp His Lys Ala Gly Val Arg Ile Thr Lys
    210                 215                 220

Glu Asp Asn Lys Gly Thr Ile Ser His Asp Val Ser Glu Phe Lys Ile
225                 230                 235                 240

Thr Lys Glu Gln Ile Ser Leu Lys Glu Leu Asp Phe Lys Leu Arg Lys
                245                 250                 255

Gln Leu Ile Glu Lys Asn Asn Leu Tyr Gly Asn Val Gly Ser Gly Lys
            260                 265                 270

Ile Val Ile Lys Met Lys Asn Gly Gly Lys Tyr Thr Phe Glu Leu His
            275                 280                 285

Lys Lys Leu Gln Glu Asn Arg Met Ala Asp Val Ile Asp Gly Thr Asn
    290                 295                 300

Ile Asp Asn Ile Glu Val Asn Ile Lys
305                 310
```